United States Patent [19]

Bamford et al.

[11] Patent Number: 5,453,467
[45] Date of Patent: Sep. 26, 1995

[54] POLYMER TREATMENTS

[75] Inventors: Clement H. Bamford; Kadem G. Al-Lamee, both of Liverpool; Yiannakis Yianni; Martin C. Wiles, both of Uxbridge; Trevor O. Glasbey, Nottingham, all of Great Britain

[73] Assignee: Biocompatibles Limited, Uxbridge, Great Britain

[21] Appl. No.: 199,285

[22] Filed: Apr. 28, 1994

[30] Foreign Application Priority Data

Aug. 30, 1991 [GB] United Kingdom ............ 9118597

[51] Int. Cl.$^6$ .............. C08F 4/52; C08F 255/02; C08F 259/08; C08F 283/04
[52] U.S. Cl. .............. 525/287; 427/2.24; 525/245; 525/276; 525/322; 525/422; 525/426; 525/455; 525/535; 525/540
[58] Field of Search .............. 427/2.24; 525/287, 525/303, 54.3, 276, 426, 455, 422, 535, 540, 245, 322

[56] References Cited

U.S. PATENT DOCUMENTS 4,792,599  12/1988  Durrani .................. 528/272

FOREIGN PATENT DOCUMENTS

| 0032622 | 7/1981 | European Pat. Off. . |
| 0157469 | 10/1985 | European Pat. Off. . |
| 54-63025 | 7/1979 | Japan . |
| 9009384 | 8/1980 | WIPO . |
| WO9300391 | 1/1993 | WIPO . |

OTHER PUBLICATIONS

Park, Soo Min, "Studies on biocompatible membranes", *Han'guk Somyu Konghakhoechi*, vol. 29, No. 10 (1992), pp. 726–731.
Sakurai et al., "Structure of the condensed phase of methacrylic copolymers with lipidic side chains", *Macromolecules*, vol. 25 (1992), p. 7256.
Biomaterials (1991), vol. 12, Mar., *Interaction Between Phospholipids and Biocompatible Polymers Containing a Phosphorylcholine Moiety.*
Bioindustry 8(6), 412–420 (1991) by Nakabayashi and a prepared English translation of the same.

*Primary Examiner*—Vasu S. Jagannathan
*Attorney, Agent, or Firm*—Sughrue, Mion, Zinn, Macpeak & Seas

[57]  ABSTRACT

A graft polymer obtainable by grafting a polymer substrate with a compound of formula (I), in which the groups R are the same or different and each is a straight or branched $C_1$–$C_4$ alkyl group; X is an aryl group or a straight or branched $C_1$–$C_{20}$ alkylene group, optionally containing one or more carbon-carbon double or triple bonds, ether linkages or aryl groups; the aryl groups being unsubstituted or substituted by one or more $C_{1-4}$ alkyl groups; n is from 2 to 4; and A is a reactive group, is useful as a biocompatible material in contact lenses, biomedical devices and blood-containing devices. In a preferred embodiment A is a polymerizable group and the graft polymer is produced by radical initiated polymerization of the compound of formula (I) on the substrate which is initiated by a radical-forming group on the substrate.

23 Claims, No Drawings

POLYMER TREATMENTS

The present invention relates to new graft polymers, processes for producing them, shaped articles having a surface comprising them and processes for biocompatabilising surfaces using them.

In modern medicine the use of blood-contacting devices is now common in many fields. Devices such as heart valves, blood vessel protheses and balloon pumps are implanted by surgical techniques. Blood-contact devices are also employed routinely outside the body, for example in blood detoxification.

Devices constructed from metals or polymeric materials will in many cases cause an adverse reaction when contacted with blood. This reaction can be caused by, for example, protein deposition or platelet (thrombocyte) adhesion and aggregation which can lead to the formation of a haemostatic plug (thrombus). Such a haemostatic reaction can have severe adverse consequences for patients.

There has been a considerable effort to develop new materials which do not provoke such an adverse reaction and are therefore considered to be biocompatible. However the need to develop effective materials in this respect still remains.

We have now devised a new series of polymers which show surprisingly increased biocompatibility and/or improved mechanical or chemical properties over known polymers. In particular the polymers of the present invention show decreased adhesion of platelets and also proteins compared to conventional polymers. They also show desirable properties in terms of increased wettability, lubricity and anti-static properties compared to conventional polymers.

The present invention therefore provides a graft polymer obtainable by grafting a polymer substrate with a compound of the formula (I):

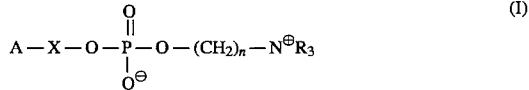

(I)

in which the groups R are the same or different and each is a straight or branched $C_1$–$C_4$ alkyl group;

X is an aryl group or a straight or branched $C_1$–$C_{20}$ alkylene group, optionally containing one or more carbon-carbon double or triple bonds, ether linkages or aryl groups; the aryl groups being unsubstituted or substituted by one or more $C_{1-4}$ alkyl groups;

n is from 2 to 4; and

A is a reactive group.

The polymers of the invention therefore comprise a polymer substrate grafted with residues of a compound of the formula (I).

In a particular embodiment, the polymers of the invention are obtainable by radical initiated grafting of the compound of formula (I) to the polymer substrate. In such a case, the reaction may be initiated by formation of a radical on the substrate which reacts with the reactive group A in the compound of formula (I). Alternatively reaction initiated by transformation of the group A in the compound of formula (I) into a radical and then reaction with a reactive group at the substrate, such as for example an ethylenically unsaturated moiety.

According to a particular aspect of the invention A is a reactive group other than:

(i) an epoxy group for example

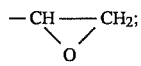

(ii) a group A'C(O)O— in which A' is a $C_{1-4}$ straight or branched alkyl group optionally substituted with one or more electron withdrawing groups (e.g. halo, nitro or cyano) or A' is an optionally substituted aromatic ring system, for example p-nitrophenyl or, an optionally substituted heteroaromatic ring system, for example imidazole;

(iii) a group $A^2OC(O)O$— where $A^2$ is an optionally substituted aromatic or heteroaromatic ring system or an N-substituted imide derivative, for example succinimide;

(iv) a group $A^3S(O)_2O$— where $A^3$ is a straight chain alkyl of 1 to 4 carbon atoms, optionally substituted by alkyl or alkoxy of 1 to 4 carbon atoms or halogen, or is an optionally substituted aromatic or heteroaromatic ring system;

(v) a group $A^4C(O)$— where $A^4$ is a halogen atom, an N-substituted nitrogen-containing heteroaromatic ring system, for example imidazole, or (vi) a group of formula $A^5$—C(O)—O—C(O)— where $A^5$ is a group

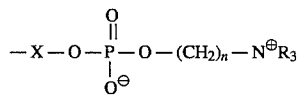

wherein R, X and n are as hereinbefore defined or $A^5$ is an alkyl group, optionally substituted by alkyl or alkoxy of 1 to 4 carbon atoms or halogen or is an optionally substituted aromatic or heteroaromatic ring system.

According to a further particular aspect of the invention, A is a reactive group other than (i) an epoxy group, (ii) a group $A^1C(O)O$— in which $A^1$ is an imidazole group, or (iii) a group $A^2OC(O)$— in which $A^2$ is a succinimido or pentafluorophenyl group.

According to another particular aspect, the invention relates to polymers which are obtainable by grafting a surface-treated polymer with a compound of formula (I); such a surface treatment may for instance graft on to the polymer compounds containing reactive linking groups. Alternatively, the polymer may comprise suitable reactive surface groups without the need for a prior surface treatment. Suitable reactive groups at a polymer surface include amino, carboxyl, isocyanate, halide, haloalkyl and vinyl groups. Alternatively, such groups may be hydroxyl, silyloxy, imido or imine groups.

In the compounds of formula (I), all the R groups are preferably the same but compounds where the R groups are different are usable. Also preferred are those compounds where the R groups are straight chain alkyl groups, i.e. methyl, ethyl, n-propyl or n-butyl most preferably methyl.

Most preferably all the groups R are methyl groups and n is 2, in which case the compounds of formula (I) are phosphoryl choline derivatives.

Preferably X is a group of formula —(CH$_2$)$_a$—, —(CH$_2$CH$_2$O)$_b$— or —(CH$_2$)$_c$Ar(CH$_2$)$_d$—, where a is from 1 to 20, e.g. 1 to 8, b is from 1 to 20, e.g. 1 to 7, and c and d are the same or different and are from 0 to 5 and Ar is an aryl group, such as a para- or meta- (preferably para-) disubstituted phenyl group which is optionally further substituted by one or more $C_{1-4}$ alkyl groups, e.g. para-disubstituted phenyl (p-$C_6H_4$).

Particular examples of aryl-containing groups X are —$CH_2$(p—$C_6H_4$)$CH_2$—, —$CH_2$(p—$C_6H_4$)—, —(p—$C_6H_4$)$CH_2$—, and —(p—$C_6H_4$)—.

The reactive group A may be a group capable of reacting with an unactivated polymer, or it may be a group capable of reacting with a reactive linking group grafted onto the polymer so as to render the polymer susceptible to reaction with the compound of formula (I).

For example A may be amino, hydroxyl, a group $HOCH_2CH(OH)$— (in which case X is preferably $CH_2$, so that the compound of formula (I) is a glycerophosphate), or an imidazolide group:

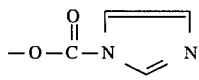

Preferably however the group A is capable of radical initiated polymerisation in which case the polymer substrate will bear radical-forming reactive groups or be grafted with radical-forming reactive linking groups, which initiate polymerisation of the compound of formula (I). This results in polymerisation of the compound of formula (I) which is initiated by the reactive groups born by or grafted to the polymer. Where A is a radical polymerisable group preferably this is an ethylenically unsaturated group, more preferably a vinyl-containing group, such a methacrylate, acrylate or styrene derived group. Groups of formula (IIA) and (IIB) provide particular examples of such groups. Groups of formula (IIA) are most preferred.

Groups of formula (IIA) are:

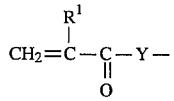
(IIA)

wherein $R^1$ is hydrogen or more preferably straight or branched $C_1$-$C_4$ alkyl, e.g. methyl, and Y is —O—, —$NR^2$— where $R^2$ is hydrogen or straight or branched $C_1$-$C_4$ alkyl or $R^2$ is a group:

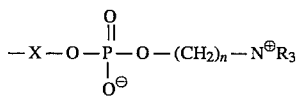
(II)

wherein X, R and n areas hereinbefore defined. Groups of formula (IIB) are:

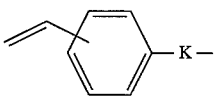
(IIB)

wherein:

K is a group —$(CH_2)_qOC(O)$—, —$(CH_2)_qC(O)O$—, —$(CH_2)_qOC(O)O$—, —$(CH_2)_qNR^3$—, —$(CH_2)_qNR^3C(O)$—, —$(CH_2)_qC(O)NR^3$—, —$(CH_2)_qNR^3C(O)O$—, —$(CH_2)_qOC(O)NR^3$—, —$(CH_2)_qNR^3C(O)NR^3$—, —$(CH_2)_qO$—, —$(CH_2)_qSO_3$—, or a valence bond and q is from 0 to 12 and $R^3$ is hydrogen or a $C_1$-$C_4$ alkyl group.

Where K is a group —$(CH_2)_qNR^3C(O)NR^3$—, the groups $R^3$ may be the same or different.

Preferably, in the groups of formula (IIB) K is a valence bond. Where K is a group then preferably q is from 1 to 6, more preferably 1, 2 or 3 and most preferably q is 1. When K is a group —$(CH_2)_qNR^3$—, —$(CH_2)_qNR^3C(O)$—, —$(CH_2)_qC(O)NR^3$—, —$(CH_2)_qNR^3C(O)O$—$(CH_2)_qOC(O)NR^3$— or —$(CH_2)_qNR^3C(O)NR^3$— then $R^3$ is preferably hydrogen, methyl or ethyl, more preferably hydrogen.

Of the compounds containing groups of formula (IIA) and (IIB), those containing groups of formula (IIA) are more preferred.

Most preferably the compound of formula (I) is 2(methacryloyloxy)-ethyl-2'(trimethylammonium)ethyl phosphate inner salt (HEMA-PC).

Polymerisation of compounds of formula (I) initiated on the polymer substrate results in a comb structure where the polymer chains bear multiple polymeric grafted pendant chains having phosphate ester side chains. The concentration of phosphate ester side chains can be reduced by copolymerising with a diluent monomer. Thus the polymer substrate is grafted with polymer chains comprising residues of a compound of formula (I) and optionally residues of diluent comonomer.

A diluent comonomer may be of any known conventional, radical polymerisable, preferably ethylenically unsaturated, type. A single diluent comonomer or alternatively more than one type of diluent comonomer may be used.

Examples of diluent comonomers include alkyl(alk)acrylate preferably containing 1 to 4 carbon atoms in the alkyl group of the ester moiety, such as methyl(alk)acrylate; a dialkylamino alkyl(alk)acrylate, preferably containing 1 to 4 carbon atoms in each alkyl moiety of the amine and 1 to 4 carbon atoms in the alkylene chain, e.g., 2-(dimethylamino)ethyl(alk)acrylate; an alkyl(alk)acrylamide preferably containing 1 to 4 carbon atoms in the alkyl group of the amide moiety; a hydroxyalkyl (alk)acrylate preferably containing from 1 to 4 carbon atoms in the hydroxyalkyl moiety, e.g., a 2-hydroxyethyl(alk)acrylate; or a vinyl monomer such as an N-vinyl lactam, preferably containing from 5 to 7 atoms in the lactam ring, for instance vinyl pyrrolidone; styrene or a styrene derivative which for example is substituted on the phenyl ring by one or more alkyl groups containing from 1 to 6, preferably 1 to 4, carbon atoms, and/or by one or more halogen, such as fluorine atoms, e.g. (pentafluorophenyl)styrene.

It is to be understood that throughout the specification (alk)acrylate, (alk)acrylic and (alk)acrylamide mean acrylate or alkacrylate, acrylic or alkacrylic and acrylamide or alkacrylamide respectively. Preferably unless otherwise stated alkacrylate, alkacrylic and alkacrylamide groups contain from 1 to 4 carbon atoms in the alkyl group thereof and are most preferably methacrylate, methacrylic or methacrylamide groups. Similarly (meth)acrylate, (meth)acrylic and (meth)acrylamide shall be understood to mean acrylate or methacrylate, acrylic or methacrylic and acrylamide or methacrylamide respectively.

Further diluents which may be mentioned specifically include alkylene anhydrides such as maleic anhydride and cyano-substituted alkylenes, such as acrylonitrile.

Provided reaction is not initiated by the formation of radicals so as to graft to hydroxyl groups, on the substrate other suitable diluent comonomers include polyhydroxyl, for example sugar, (alk)acrylates and (alk)acrylamides in which the alkyl group contains from 1 to 4 carbon atoms, e.g. sugar acrylates, methacrylates, ethacrylates, acrylamides, methacrylamides and ethacrylamides. Suitable sugars include glucose and sorbitol. Particularly suitable diluent comonomers include methacryloyl glucose or sorbitol methacrylate.

In addition, diluent comonomers may be used which provide crosslinking between polymer chains. Suitable crosslinking comonomers include diol (e.g. ethylene glycol) diacrylates or dialkacrylates (e.g. dimethacrylates) containing 1 to 4 carbon atoms in the diol, and in the alkyl group of the alkacrylate if present. Especially preferred is ethylene glycol dimethacrylate.

Diluent comomoners may be obtained by conventional known methods.

The present invention may be applied to many known polymer types as substrate, especially those used in manufacture of bio-medical apparatus, contact lenses and blood-contacting devices, such as:

hydroxy alkyl acrylate or alkacrylate, (e.g. methacrylate) hydrogels for example, hydroxyethylmethacrylate (HEMA) hydrogels or hydroxyethyl methacrylate/ methacrylic acid (HEMA/MA) hydrogels, cellulose and cellulose derivatives such as Cuprophan, cellulose acetate and cellulose nitrate, polyvinyldifluoride (PVDF), polyamides (e.g. nylons), polyimides.

Other polymers which may be treated in accordance with the present invention include polyurethanes, polyimines and polyethersulphones.

In addition, the present invention may be applied to the treatment of polymeric subbing layers laid down on polymeric and non-polymeric substrates such as silicone rubber and stainless steel, and also glass. Preferred materials for use as subbing layers include hydroxy (alk)acrylates, more preferably HEMA, and functionalised polyimines, for example halogenated polyethyleneimine silane.

In many cases a compound of formula (I) may be grafted onto the polymer by grafting to a reactive group on the polymer molecule such as a hydroxyl or halo group. For example, compounds of formula (I) in which A is an ethylenically unsaturated polymerisable group may be grafted onto a polymer molecule or surface using radical initiated polymerisation of the compound of formula (I). Suitable polymers and surfaces for grafting in this manner include HEMA, HEMA/methacrylic acid, cuprophan, cellulose acetate, PVDF, polypropylene, nitrocellulose, polyamide and trialkyloxysilylalkyl methacrylate surfaces. Initiation may be provided conventionally, such as with a Ce(IV) salt (e.g. cerium ammonium nitrate) or a persulphate, (e.g. ammonium or alkali metal persulphate) optionally in combination with or mild reducing agent such as a thiosulphate (e.g. sodium thiosulphate), azobiscyanovaleric acid or by heating with a catalyst for example molybdenum or tungsten, preferably molybdenum hexacarbonyl. Alternatively, initiation may be provided by irradiation with actinic, preferably u.v. or gamma-irradiation, preferably in the presence of a catalyst such as a metal carbonyl, for example dimanganese or dirhenium, more preferably dirhenium, decacarbonyl.

Preferred radical initiators include cerium (IV) salts, and metal carbonyls, in particular molybdenum or tungsten carbonyl (when reaction is thermally initiated) or dirhenium or dimanganese decacarbonyl (when reaction is photochemically initiated).

When grafting is to a hydroxyl group Ce(IV) salts are preferred as initiators. When grafting is to a position occupied by a halogen atom, thermal initiation with molybdenum hexacarbonyl is preferred. Also preferred, when grafting via a position occupied by a halogen atom, is initiation by irradiation in the presence of dirhenium decacarbonyl.

Without being bound by theory, the Applicants believe that in such cases polymerisation is initiation by the generation of a radical at a reactive group bound to the polymer. Polymerisation of the compound of formula (I) then occurs by reaction with the polymer-bound radical.

Reactive groups may be present on the polymer substrate without requiring pre-treatment, e.g. the hydroxyl groups in HEMA or in cellulose derivatives. Alternatively reactive groups, such as hydroxyl groups, may be introduced by pre-treatment such as by oxygen plasma treatment or oxidation, e.g. with a peracid such as peracetic acid, or with ozone. In cases, such as polypropylene, where there are no reactive groups in the polymer, or groups to which a linking group may beattached, it may be necessary to use plasma polymerisation or oxidation prior to grafting.

In cases where the substrate is pre-treated by laying down a subbing layer, then the subbing layer is generally laid down following plasma etching to activate the substrate surface. Subbing layers may be formed of any suitable polymer which may be treated as described above or in what follows. Subbing layers may for example be formed of a functionalised polyimine, such as halogenated polyethylene imine, or more preferably, a hydroxyalkyl acrylate or alkacrylate (e.g. methacrylate), such as HEMA, or of a trialkyloxy silylalkyl (e.g. trimethoxysilyl) acrylate or alkacrylate (e.g. methacrylate), for instance 3-(trimethoxysilyl)propyl methacrylate. Alternatively, a subbing layer comprising a mixture of two monomers may be used, for instance a mixture of HEMA and HEMA-PC. Use of such a mixture can facilitate reaction at the subbing layer on the substrate, in some solvents, for example water.

A combination of more than one subbing layer may be used, for example a layer of trialkylsilyl alkyl acrylate or alkacrylate followed by a layer of hydroxylalkyl acrylate or alkacrylate. Use of such a combination, and in particular, the combination of silyl methacrylate and HEMA can give significantly improved results in terms of biocompatibility compared to use of a single subbing layer of for example, silylmethacrylate. Thus grafting of HEMA-PC onto a combination of these two subbing layers using ceric initiation is superior to grafting onto a silylmethacrylate subbing layer. Typically in these acrylates or alkacrylates all alkyl groups contain from 1 to 4 carbon atoms.

The invention will be described below with particular reference to treatment of polyurethane. However, these techniques can also be applied to many other polymeric materials, such as those mentioned including polymeric subbing layers.

In a particular aspect, the polymer of the present invention comprises grafted groups, which are grafted to the nitrogen atoms of the —NHCO— groups of a polyurethane chain. Most particularly, all of the grafted groups are grafted to such nitrogen atoms.

In a particular aspect the invention provides polymers, e.g. polyurethanes, comprising a group of the formula (III)

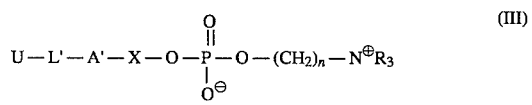

in which X, R and n are as hereinbefore defined, U is a portion of a polymer, e.g. polyurethane, chain, L' is a linking group and A' is the residue of a reactive group A as hereinbefore defined, obtainable by reaction with a group L grafted onto a polymer, e.g. a polyurethane, or with a group L graftable onto a polyurethane, provided that when U is a polyurethane the group of formula (III) is other than

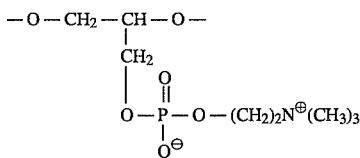

Preferably the group of formula (III) is other than the residue of a diol or polyol having at least two reactive groups capable of reacting with an isocyanate group and having the residue of at least a further hydroxyl group present in the form of a phosphorus acid ester of formula

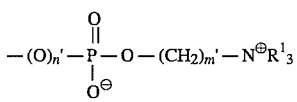

where n' is 0 or 1, m' is 1, 2, 3 or 4 and R independently is an alkyl group containing 1 to 4 carbon atoms.

L may be any sort of conventional group which may be grafted onto a polymer, such as a polyurethane. The group L may comprise one or more isocyanate groups, particularly if U is a polyurethane fragment.

If U is a portion of a polyurethane chain, the group of formula (III) comprises a group grafted to the nitrogen atom of an —NHCO— moiety in the polyurethane chain, so that U is a group:

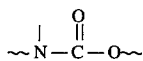

In a first embodiment, L' may for example be a group of formula:

 (IVA)

 (IVB)

where the —CONH moiety is directly attached to the polymer, e.g. polyurethane, chain and; in which $R^4$ or is an aryl group or a straight or branched $C_1$–$C_{20}$ alkylene chain, which optionally contains one or more ether linkages, carbon-carbon double or triple bonds or aryl groups and is unsubstituted or substituted by one or more halogen atoms. When $R^4$ or $R^5$ is or comprises an aryl group, the aryl group is preferably a para- or meta-disubstituted phenyl group which is optionally further substituted by one or more $C_{1-4}$ alkyl groups.

Preferably $R^4$ and $R^5$ are the same or different and each is —$(CH_2)_{1-10}$—, e.g. —$(CH_2)_{2-6}$— unsubstituted or substituted by one or more halogen atoms, or a disubstituted m-phenyl group, which is optionally further substituted by one or more $C_1$–$C_4$ alkyl groups, e.g. methyl groups or halogen atoms. Preferably $R^5$ is a methylene or ethylene group, unsubstituted or substituted by one or more chlorine atoms on the carbon atom directly bonded to A'.

If L' is a group (IVA) or (IVB), A' is typically —NH— or —O—.

In a second embodiment L' may be a polymeric group, in which for instance the group L' is linked to A' by —NHCO- (amido) or —CO-(carbonyl) side-linkages from the polymer chain. In such cases —A'—X—, is typically a group —OCH$_2$—CH(OH)—X—, or —NH—X—, or —O—X— when the linkage is an amido linkage or —O—X— where the linkage is a carbonyl linkage.

Where L' is a polymeric group it may be, for instance, a polymer or copolymer of:

(i) an ethylenically unsaturated compound containing an amino group, such as a compound of formula (V)

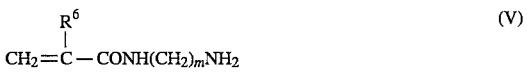 (V)

where $R^6$ is $C_1$–$C_4$ alkyl, e.g. methyl, m is from 1 to 10, (e.g. 3 to 6) where the L'—A' linkage is via an amido group;

(ii) an ethylenically unsaturated compound containing an isocyanate group, such as a compound of formula (VI):

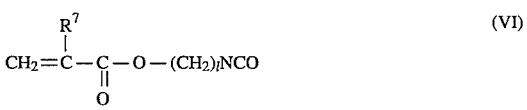 (VI)

where $R^7$ is hydrogen or $C_1$–$C_4$ alkyl, e.g. methyl, and l is from 1 to 10, for instance 1 to 4, e.g. 1 when the L'—A' linkage is via an amido group; or (iii) an ethylenically unsaturated compound containing a carboxyl group, such as a compound of formula (VII):

 (VII)

where $R^8$ is hydrogen or $C_1$–$C_4$ alkyl e.g. methyl, and k is from 0 to 10, for instance 0 to 4, where the L'—A' is via a carbonyl group.

Particular examples of the compounds of formulae (VI) and (VII) include 2-isocyanatoethyl methacrylate and methacrylic acid respectively.

The concentration of pendant reactive groups, such as amino, isocyanato or carboxyl groups in a polymeric group L' may be varied by use of a copolymer of an ethylenically unsaturated monomer containing such groups and a diluent ethylenically unsaturated comonomer. In this respect, the same diluent comonomer may be used as those mentioned as diluent comonomer for use with compounds containing a group of formula (IIA) or (IIB) above.

In another, and more preferred, aspect, the present invention provides polymers, e.g. polyurethanes, comprising a group of formula (VIII).

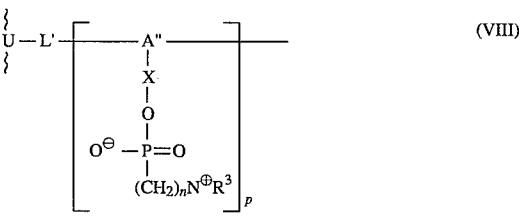 (VIII)

where p is 2 or more for instance up to 2×10$^7$, preferably 10,000 to 1,000,000, and A" is the residue of an ethylenically unsaturated moiety and L', X, n and R are as hereinbefore defined In particular A" may be the residue of a group of formula (IIA) or (IIB) as hereinbefore defined.

If U is a portion of a polyurethane chain the group of formula (VIII) comprises a group grafted to the nitrogen atom of an —NHCO— moiety in the polyurethane chain so that U is a group:

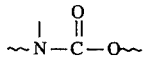

In this embodiment —L'— may for example be the residue of a radical forming linking group —L—. Alternatively, the polymerisation may be initiated in such a way as to graft the compound of formula (I) direct to the polymer chain.

L' may for example be a group of formula (IX):

—COHNR$^9$NHCONHR$^{10}$— (IXA)

—CONHR$^{11}$OC(=O)— (IXB)

—CONHR$^{12}$— or (IXC)

—CONHCOR$^{13}$ (IXD)

in which $R^9$ and $R^{10}$, or $R^{11}$ are an aryl group or a straight or branched $C_1$–$C_{20}$ alkylene chain, which optionally contains one or more ether linkages, carbon-carbon double or triple bonds or aryl groups and is unsubstituted or substituted by one or more halogen atoms.

When $R^9$, $R^{10}$ or $R^{11}$ is or comprises an aryl group, the aryl group is preferably a para- or meta-disubstituted phenyl group which is optionally further substituted by one or more $C_{1-4}$ alkyl groups.

Preferably $R^9$, $R^{10}$ and $R^{11}$ are —(CH$_2$)$_{1-10}$—, e.g. —(CH$_2$)$_{2-6}$— unsubstituted or substituted by one or more halogen atoms, or a disubstituted m-phenyl group, which is optionally further substituted by one or more $C_1$–$C_4$ alkyl groups, e.g. methyl groups or halogen atoms. Preferably $R^{12}$ or $R^{13}$ is a methylene or ethylene group, unsubstituted or substituted by one or more chlorine atoms on the carbon atom directly bonded to A'.

The present invention also provides a process for producing a graft polymer which comprises grafting to a polymer substrate, a group of the formula (X):

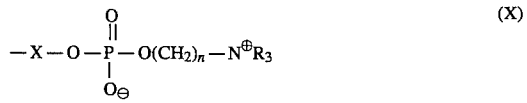

in which X, n, and R are as hereinbefore defined.

The process of the present invention may be performed in solution or, more preferably, by grafting to the surface of a polymer substrate. Preferably, the process will be carried out so as to ensure that the surface is grafted with sufficient groups of formula (X) so that, when exposed to fibrinogen, in accordance with the procedure of the assay for fibrinogen absorption described hereinafter, the surface absorbs no more than 10 ng/cm$^2$ of fibrinogen.

The grafting reaction may be performed using any methods known for the grafting to a polymer substrate. In a particular aspect it may be performed by the use of a linking group L' according to the reaction:

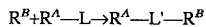

where either (a) $R^A$ is a substrate and $R^B$ is a compound of formula (I), or (b) $R^A$ is the residue of a compound of formula (I) and $R^B$ is a substrate.

Preparation of Compounds Containing a Group (IVA)

Grafted polymers, such as polyurethanes, comprising groups of formula (III), where L' is a group —CONHR$^4$NHCO— may be obtained by reacting a polymer substrate $R^A$—L in which L is a group —CONHR$^4$NCO with, as $R^B$, a compound of formula (I) in which A is a hydroxyl or amino group. Alternatively such polymers may be obtained by reaction of, as $R^B$, polymer with a compound $R^A$—L in which L is a group —CONHR$^4$NCO and $R^A$ is the residue of a compound of formula (I) in which A is a hydroxyl or amino group.

In either case the reaction is typically performed in solution, in an organic medium, e.g. a mixture of dimethylacetamide and dimethylsulphoxide or dimethyl formamide and at a temperature from −10° to 100° C., e.g. 0 to 50° C. the reaction may be performed in the presence of a catalyst, such as a tertiary amine (e.g. triethylamine) or an organometallic compound, such as stannous octoate.

When $R^A$ is a polymer, such as a polyurethane, $R^A$—L may be obtained by the reaction of polymer with a diisocyanate of formula (XI)

in which $R^4$ is as hereinbefore defined.

This reaction may be performed using conditions similar to those for the reaction of $R^A$—L with $R^B$.

When $R^A$ is the residue of a compound of formula (I), $R^A$—L may for example be obtained by reaction with a diisocyanate of formula (XI) in an organic medium, e.g. dimethyl formamide at a temperature from 15° to 30° C.

Preparation of Compounds Containing a Group (IVB)

Grafted polymers, such as polyurethanes, comprising groups of formula (III), in which L' is a group of formula —CONHR$^5$— may be obtained by reacting a polymer substrate $R^A$—L where L is CONHR$^5$—Z in which Z is halogen e.g. chlorine or another readily displaceable group e.g. p-toluenesulphonyl (tosyl) or methanesulphonyl (mesyl), with a compound $R^B$ of formula (I) in which A is hydroxyl or amino.

Reaction with compounds of formula (I) in which A is hydroxyl may be performed by converting the hydroxide to an alkoxide for instance by reaction with potassium hydroxide or potassium t-butoxide in the presence of 18-crown-6. Reaction with compounds of formula (I) in which A is amino may be performed with an excess of amine, preferably in the preference of a catalytic amount of potassium iodide.

Alternatively, grafted polymers, such as polyurethanes, comprising groups of formula (III), in which L' is a group of formula —CONHR$^5$— may be obtained by reacting a polymer substrate, $R^B$, with a compound $R^A$—L where L is —R$^5$NCO, and $R^A$ is the residue of a compound of formula (I). This reaction may be performed in solution in an organic solvent, e.g. a mixture of dimethylacetamide with dimethylsulphoxide or dimethyl formamide at a temperature from 0° to 50° C. The reaction may be performed in the presence of a catalyst, e.g. a tertiary amine such as triethylamine or an organometallic catalyst such as stannous octoate.

The compound $R^A$—$R^5$—NCO may be obtained by reaction of a compound of formula (I) in which A is a hydroxyl or amino group with a compound of formula (XII)

OCN—$R^5$—NCO (XII)

The reaction may be carried out in a non-protic solvent such as acetonitrile and is typically performed using an excess of di-isocyanate (XI)

Preparations of Compounds Containing a Group (IXA)

Grafted polymers, such as polyurethanes, comprising groups of formula (VII) in which L' is a group —CONHR$^9$NHCONHR$^{10}$— may be obtained by reaction of a polymer substrate $R^A$—L, in which L is —CONHR$^9$NHCONHR$^{10}$OH with a compound $R^B$ which contains a polymerisable group such as a group of formula (IIA) or (IIB) in the presence of a redox initiator. The reaction occurs with radical initiated in situ polymerisation of the compound of formula (I), containing a polymerisable group. The reaction is preferably performed in an aqueous environment and in the presence of Cerium (IV), as a redox initiator.

The polymer $R^A$—CONHR$^9$NHCONHR$^{10}$OH may be obtained by reaction of a polymer formula $R^A$—CONHR$^9$NCO, whose preparation is described above in relation to $R^A$—CONHR$^4$NCO, with a compound H$_2$NR$^{10}$OH. This reaction may be carried out at room temperature, e.g. 10° to 30° C., in an organic solvent such as dichloromethane or acetonitrile, or in some cases, such as if H$_2$N—R$^{10}$—OH is ethanolamine, in the absence of solvent.

Preparation of Compounds Containing Group (IXB)

Grafted polymers, such as polyurethanes, comprising groups of formula (VIII) where L' is a group of formula —CONHR$^{11}$OC(=O)—, may be obtained by reacting a polymer substrate $R^A$—L where L is —CONHR$^{11}$OC(=O)R$^{14}$, in which R$^{14}$ is a carbon-carbon double bond containing group, with a compound $R^B$ which is a compound of formula (I) containing a polymerisable group such as a group of formula (IIA) or (IIB) in the present of a radical initiator. This reaction occurs with in situ polymerisation of the compound of formula (I) containing a polymerisable group. Preferably the group R$^{14}$ contains a terminal carbon-carbon double bond, such as

where R$^{15a}$ is C$_1$–C$_4$ alkyl, e.g. methyl, or alternatively R$^{15}$ is a hydrogen.

In particular a copolymer with 2-hydroxyethylmethacrylate may be used.

The reaction may be carried out in the presence of an initiator, such as azobisisobutyronitrile (AIBN) and at a temperature from 15° to 70° C., e.g. about 60° C. The copolymer will typically be dissolved in an organic solvent, e.g. methanol and reacts at the surface of the polymer substrate.

The compound $R^A$—CONHR$^{11}$OC(=O)R$^{14}$ may be obtained by reaction of a polymer with a compound of formula (XIII)

OCN—R$^{11}$—OC(=O)R$^{14}$ (XIII)

in which R$^{11}$ and R$^{14}$ are as hereinbefore defined.

This reaction may be conducted for example using a solution of the compound of formula (XIII) in an organic solvent, e.g. hexane at the surface of the polymer. The temperature may for example be from 15° to 30° C.

Preparation of Compounds Containing a Group (IXC) or (IXD)

Grafted polymers, such as polyurethanes, comprising groups of formula (VIII), in which L' is —CONHR$^{12}$ or —CONHCOR$^{13}$— may be obtained by reacting a polymer substrate $R^A$—L' where L is —CONHR$^{12}$Hal or —CONHCOR$^{13}$Hal in which Hal is halogen, e.g. chlorine, with a compound of formula (I) containing a polymerisable group, such as a group of formula (IIA) or (IIB) in the presence of a radical initiator. This reaction occurs with in situ polymerisation of the compound of formula (I) containing a polymerisable group.

The reaction is usually performed at the surface of the substrate, using a solution of monomer in an organic solvent, e.g. a mixture of methanol and ethyl acetate or DMF as described by Bamford etal, Bull. Soc. Chim. Belg. (1990), Vol 99, 919–930. The reaction is typically performed photochemically in the presence of a radical initator e.g. dirhenium or dimanganese decacarbonyl. Where dirhenium decarbonyl is used as an initator radiation having a wavelength of about 365 nm is typically used, and where dimanganese decacarbonyl is used radiation having a wavelength of about 436 nm is typically used. Alternatively the reaction can be performed thermally, e.g. in the presence of a metal carbonyl such as molybdenum or tungsten carbonyl and at a temperature from 40°–120° C. e.g. about 60° C.

Polymers $R^A$—CONHR$^{12}$Hal may be obtained as described above for the compounds $R^A$—CONR$^5$—Z. Among such compounds use of those in which R$^{12}$Hal is CHal$_3$, CH.Hal$_2$, CH$_2$Hal, or CH$_2$CH$_2$Hal is preferred.

Polymers $R^A$—CONHCOR$^{13}$Hal may be obtained by reaction of a polyurethane with a compound of formula (XIV)

in which R$^{13}$ and Hal are as hereinbefore defined. Among such compounds use of those in which R$^{12}$ Hal is CHal$_3$, CHHal$_2$, CH$_2$Hal or CH$_2$CH$_2$Hal is preferred.

The reaction may be performed at the surface of a substrate, using a solution of a compound of formula (XIV) in an organic solvent, e.g. hexane and at a temperature from −10° to 50° C.

Preparation of Compounds in which L' is polymeric a. Reaction with glycol derivative as compound of Formula (I)

Grafted polymers such as polyurethanes, comprising groups of formula (III) in which L' is a polymeric group linked by an amido (—NHCO—) linkage to A' and A' is —OCH$_2$— CH(OH)— may be obtained by reacting a polymer substrate $R^A$—L in which L is a copolymer containing amino groups with a compound of formula (I), as $R^B$, in which A is a —CH$_2$OHCH(OH)— group (and X is preferably —CH$_2$—) in the presence of a coupling agent such as a cyanogen halide. Typically L will be a polymer or copolymer of a compound of formula (V).

The reaction is generally performed in the presence of a cyanotrialkylammonium halide, salt e.g. a cyanotriethylammonium halide, as a coupling reagent, at the surface of a polymer substrate and using a basic solution of a compound of formula (I) in a solvent such as a mixture of acetone and water. Typically the compound of formula (I) is first reacted with cyanogen bromide at a temperature from −50° C. to +10° C. and is then contacted with the polymer substrate surface at a temperature from −10° to 50° C., e.g. 10° to 30° C.

b. Reaction with Amino or Alcohol as Compound of Formula (I)

Grafted polymers, such as polyurethanes, comprising groups of formula (III) in which L' is a polymeric group linked by an amido (—NHCO—) linkage to A' and A' is —NH— or —O— may be obtained by reacting a polyurethane, $R^A$—L where L is a polymer or copolymer containing isocyanate groups such as a polymer or copolymer of a compound of formula (VI) with a compound of formula (I), as $R^B$, in which A is an amino or hydroxyl group. The reaction may be carried out at the surface of a polymer substrate, using a solution of a compound of formula (I) in an organic solvent, e.g. hexane, and typically at a temperature from −10° to 50° C.

c. Reaction with Imidazolide as Compound of Formula (I)

Grafted polymers, such as polyurethanes, comprising groups of formula (III) in which L' is a polymeric group linked by carbonyl linkage to A' and A' is —O—, (i.e. together A'—L' are bonded by a carboxyl linkage), may be obtained by reacting a polymer substrate $R^A$—L, in which L is a polymer or copolymer containing amino groups such as a polymer or copolymer of a compound of formula (V), with a compound of formula (I), as $R^B$, in which A is an imidazolide group. The reaction may be carried out in an organic solvent such as acetonitrile, at room temperature, e.g. 10°–30° C.

Polymer substrates, e.g. polyurethanes, $R^A$—L, in which L is itself polymeric, may be obtained by the photochemically initiated reaction of a monomer containing amino, isocyanate or carboxyl groups, e.g. a compound of formula (V), (VI) or (VII), and optionally a diluent comonomer with a polymer, such as a polyurethane, $R^A$—L where L is —CONHR$^{12}$, —CONHCOR$^{13}$Hal, where $R^{12}$, $R^{13}$ and Hal are as hereinbefore defined. The reaction occurs with in situ polymerisation of the compound containing amino, isocyanato or carboxyl groups on the polymer. The conditions used are as those described above in relation to reaction of the compounds of formula (I), containing a polymerisable group such as a group of formula (IIA) or (IIB).

Grafted polymers, such as polyurethanes, may also be obtained by reacting oxidised polymers, such as polyurethanes, with for example a copolymer of a compound of formula (I) containing a group of formula (I). The reaction may be performed under aqueous conditions in the presence of cerium (IV) as a radical initiator.

Oxidised polymers, such as polyurethanes, may be obtained simply by exposure to air, which may produce some peroxide groups on the surface of the polymer. Alternatively oxidation may be obtained deliberately, e.g. photochemically by exposure to ultra-violet radiation in an oxygenated medium, e.g. an aqueous solution, or in air, or thermally by heating in an oxygenated aqueous medium, e.g. a solution of polymer, in the presence of a radical source such as azobiscyanovaleric acid.

The compounds of formula (I) used to obtain the polymers of the present invention may be prepared by using methods described hereinafter.

Preparation of Compounds of Formula (I) where A is $NH_2$

Compounds of formula (I), in which A is an amino group, ie compound of formula (XV)

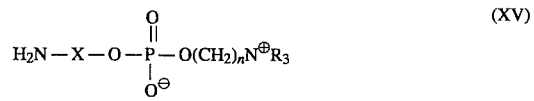

may be obtained by reacting a protected compound of formula (XVI)

in which $R^{16}$ is a protecting group and $R^{17}$ is a protecting group or hydrogen, or $R^{16}$ and $R^{17}$ together form a protecting group, or $NR^{16}R^{17}$ is $NH_3^+An^-$ in which $An^-$ is a counterion, with a compound of formula (XVII)

in which n is as hereinbefore defined and Hal is a halogen, preferably chlorine, to provide a compound of formula (XVIII)

in which $R^{16}$, $R^{17}$, X and n are as hereinbefore defined, reacting the compound of formula (XVIII) with $NR_3$, where R is as hereinbefore defined, and removing all protecting groups to provide a compound of formula (XVI).

This method is described in more detail, together with further methods for the preparation of these compounds in WO-A-92/07858 (incorporated herein by reference).

The specific details of this method are as follows:

The coupling of the N-protected alcohols of formula (XVII) to the compounds of formula (XVII) may be performed in the presence of a base under anhydrous conditions. The reaction is typically performed at a temperature from −5° to 50° C. (preferably 10° to 30° C., e.g. 25° C.) in a dry organic solvent, e.g. acetonitrile or N,N-dimethylformamide and in the presence of an organic base, such as a tertiary amine, e.g. triethylamine or pyridine, or an inorganic base, such as an alkali metal carbonate, e.g. sodium carbonate.

The ring opening reaction may, for example, be performed with a tertiary amine, e.g. trimethylamine, at a temperature from 20° to 100° C., preferably 40° to 80° C., e.g. 70° C., and in a sealed pressure vessel for 3 to 72 hours (e.g. 18 hours).

The deprotection may be performed as a separate step after or, in some cases, before the ring-opening reaction. It may also be performed at the same time as the ring-opening reaction.

The protecting groups are chosen so that they do not react with the compounds of formula (XVIII). As examples of particular protecting groups there may be mentioned:

amides ($NR^{16}$ and/or $NR^{17}$ is an amide group), e.g. N-phthalimides;

carbamates ($NR^{16}$ and/or $NR^{17}$ is a carbamate group), e.g.

9-fluorenylmethoxycarbonylamines, or tert-butyloxycarbonylamines;

hindered secondary amines, ($R^{16}$ is a hindered group e.g. triphenylmethyl and $R^{17}$ is H); or salts, ($NR^{16}R^{17}$ is a $NH_3^+An^-$ group). Suitable counter ions $An^-$ are anions of organic acids, such as acetic or p-toluene sulphonic acid or inorganic acids such as hydrogen halides, e.g. hydrogen chloride.

The N-protected aminoalcohols of formula (XVI), may be prepared from bromoalcohols of formula (XIX) or aminoalcohols of formula (XX) which are commercially available or may be prepared by known methods:

(XIX)

(XX)

In some cases, the protected amino alcohols are themselves commercially available e.g. N-(2-hydroxyethyl)phthalimide.

In the case where the protecting group is an amido the protected amino alcohol may be prepared from either the bromoalcohol of formula (XIX) or the aminoalcohol of formula (XX) by known methods. For example if the protecting group is a phthalimide, the protected amino alcohol is obtained by reaction with an alkali metal phthalimide, e.g. potassium phthalimide. Typically the reaction with phthalimide is performed in an organic solvent such as N,N-dimethylformamide at a temperature from 70° to 110° C. e.g. 90° C. After coupling to a phosphorus compound of formula (XVIII) and ring-opening, deprotection is performed under basic conditions (for example, in aqueous hydrazine). This gives the final product of formula (XVI) which can be purified for instance by column chromatography using, for example, silica gel.

In the case where the protecting group is a carbamate, protection is afforded by reaction of an amino alcohol with, for example, a chloroformate or acid anhydride to give a carbamate. The reaction is generally performed in an organic solvent, at a temperature from 10° to 50° C. and in the presence of a base. 9-Fluorenylmethoxychloroformate, for example, reacts with amines to give 9-fluorenylmethoxycarbonylamine derivatives and di-tert-butyldicarbonate reacts with amines to give tert-butyloxycarbonylamine derivatives. Ethanolamine, for example, reacts with 9-fluorenylmethoxychloroformate under anhydrous conditions in an inert solvent such as dichloromethane, in the presence of a suitable base such as pyridine, in a temperature range of, for example, −10° C. to 50° C., for example, 10° C., to give N-9-fluorenylmethoxycarbonylaminoethanol. Ethanolamine reacts with di-tert-butyldicarbonate under aqueous conditions, for example, aqueous 1,4-dioxan, in the presence of a suitable base, for example sodium hydroxide, at a suitable temperature, for example −10° C. to 50° C., preferably at 0° C., to give N-tert-butyloxycarbonyl-aminoethanol.

The carbamate protecting groups may be removed after the coupling reaction by known methods. For example the N-9-fluorenylmethoxycarbonyl amine protecting group may be removed under basic conditions in a suitable solvent, such as acetonitrile. Suitable bases for amine deprotection include ammonia, dialkylamines such as diethylamine, trialkylamines such as trimethylamine, cyclic amines and especially cyclic secondary amines such as morpholine, piperazine, piperidine and diazabicyclic bases such as 1,5-diazabicyclo(4.3.0)non-5-ene (DBN) and 1,8-diazabicyclo(5.4.0)undec-7-ene (DBU). The deprotection conditions may be chosen such that deprotection is performed prior to ring-opening or at the same time. The tert-butyloxycarbonyl amine protecting group may be removed using a suitable acid, for example trifluoroacetic acid or hydrochloric acid. The reaction may be performed in a suitable solvent system, for example, 1,4-dioxan/chloroform mixtures at a temperature of 0° to 50° C., for example, 21° C.

In the case where the protecting group is a hindered secondary amine the protected aminoalcohol (XVII) may be prepared by initial blocking of the hydroxyl function (for example, by reacting with chlorotrimethylsilane) in an organic solvent (for example, tetrahydrofuran) in the presence of an organic base (for example triethylamine). The amine function is then protected using a hindered chloroalkane (for example, chlorotriphenylmethane) in the presence of an organic base (for example, triethylamine). The hydroxyl function is then deprotected under mild conditions (for example, with methanol).

After coupling and ring opening, deprotection may be performed under acidic conditions, for example, with trifluoroacetic acid or with hydrogen chloride gas, in a non-aqueous solvent, for example, 1,4-dioxan, or chloroform. This gives the crude product which can be purified by column chromatography using, for example, silica gel.

If $NR^{16}R^{17}$ is $NH_3^+An^-$ in the protected aminoalcohol of formula (XVII), it will react with the compound of formula (XVIII) selectively via the hydroxyl group. Protected aminoalcohols in which $NR^{16}R^{17}$ is $NH_3^+An^-$ are prepared by protonation with a suitable acid. Suitable acids include inorganic and organic acids especially p-toluenesulphonic acid which gives with, for example, ethanolamine, a crystalline p-toluenesulphonate which is soluble in a solvent suitable for the reaction with (XVII), for example, acetonitrile.

After coupling, these amine salts may be converted to free amines under suitable basic conditions using, for example, trimethylamine. Advantageously, the protected amine salts are ring-opened and converted to free amines in a single step using trimethylamine. In the case where the acid addition salt is desired it is not necessary to deprotect the amine group.

Preparation of Compounds of Formula (I) where A is —OH

Compounds of formula (I) in which A is hydroxyl i.e. compounds of formula (XXI)

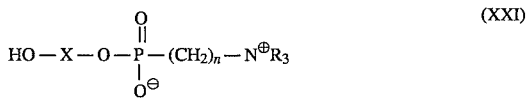

(XXI)

may be obtained by a process analogous to that used to prepare the compounds of formula (XV), but according to the following scheme A:

Scheme A

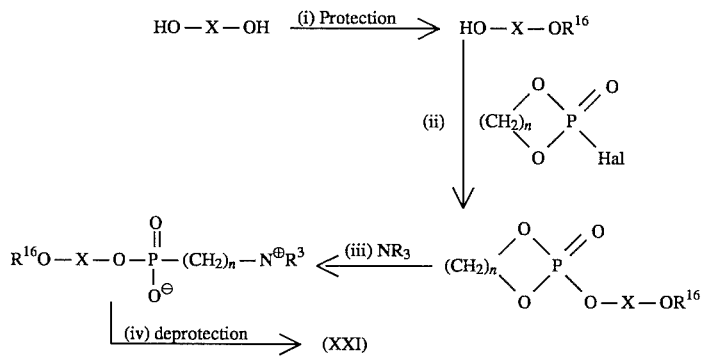

The protection step (i) may be performed using any suitable alcohol protecting group. For example a vinyl ether, e.g. ethyl vinyl ether may be used to introduce a protecting group $R^{16}$ which is —CH(CH$_3$)—OC$_2$H$_5$.

This reaction is typically performed using an organic acid such as para-toluene sulphonic acid, in an organic solvent, e.g. acetonitrile at a temperature from −20° to +40° C., e.g. about 0° C.

The steps (ii) and (iii) may be performed using the procedures described above for the preparation of compounds of formula (XVI) in relation to reaction with compounds of formula (XVIII) and with NR$^3$.

The deprotection step (iv) may be performed by known methods. For instance in the case of a vinyl ether protecting group, deprotection may be performed at room temperature using dilute hydrochloric acid.

Alternatively, compounds of formula (XXI) in which —X— is a group —CH$_2$CH$_2$—, which is unsubstituted or substituted by an alkyl group (optionally containing one or more etheric oxygen atoms) may be prepared by a process which comprises reacting a compound of the formula (XXIA):

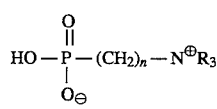

in which R and n are as hereinbefore defined, with ethylene oxide or or an alkyl substituted derivative thereof. In practice this may be performed by forming the epoxide in situ from a hydroxy compound containing a readily displaceable group alpha to the hydroxy group. This method is described in more detail in our earlier patent application no. 9119013.2, filed 5 Sep. 1991. The contents of which are incorporated herein by reference.

Preparation of Compounds of Formula (I) where A is Imidazoide

Compounds of formula (I) in which A represents an imidazolide group, i.e, compounds of formula (XXII)

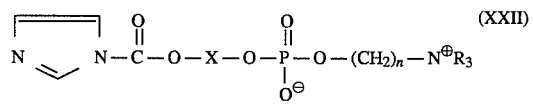

may be obtained by the reaction of compounds of formula (XVII) with carbonyl diimidazole, typically in an organic solvent, e.g. dimethylacetamide. The preparation of this type of compound is described in more detail in WO-A-91/13639, the contents of which are incorporated herein by reference.

Preparation of Compounds of Formula (I) where A is a Glycyl group

Compounds of formula (I) in which A represents a group of formula HOCH$_2$CH(OH)—, i.e. compounds of formula (XXIII)

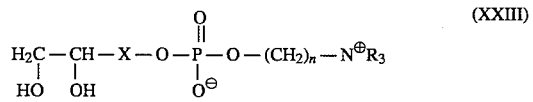

may be obtained by a procedure directly analogous to that used to prepare compounds of formula (XXI) but starting from a protected triol, (XXIV):

The compounds of formula (I) containing a polymerisable group of formula (IIA) or (IIB) may be obtained by direct analogy with the Reference Examples which describe the preparation of 2-(methacryloxyethyl)-2'-(trimethylammonium)ethyl phosphate inner salt and 1[4(4'-vinylbenzyloxy)butane-2"-(trimethylammonium)ethyl phosphate inner salt.

The polymers, such as polyurethanes, of the present invention can be used as construction material for implants or prostheses for the human or animal body, particularly where these implants or prostheses are to come into direct physical contact with blood and where biocompatibility and particularly haemocompatibility are required e.g. in heart valves where toughness or flexibility is also required, or as cement in contact lenses. They can also be used in the construction of membranes and other devices that are to be brought into contact with blood or other body fluids on an extra-corporeal basis, for example in heart-lung machines or artificial kidneys. In addition, the polymers of the present invention can be used to coat implants, prostheses, membranes, catheters, contact lenses and other devices which are constructed of another less biocompatible material but which are coated with a polymer according to the present invention to impart biocompatibility to the article. These polymers may also be used in situations where biocompatibility to cell attachment and growth is required such as in tissue culture dishes and substrates. Furthermore, polymers of this type may be used where wettability characteristics e.g. with sea water may be necessary.

Accordingly the invention provides a shaped article having one or more surfaces comprising a polymer, of the present invention. Such an article may in a particular aspect be a biomedical device, a contact lens or a blood-contacting device.

PVDF, polyamides, polyimides and subbing layers on other substrates. Those polymers which may readily be dissolved in inert solvents may also be treated in solution to afford a material grafted in bulk:such materials are particularly useful in production of devices where surface abrasion is likely or which are formed by machining the polymer.

The present invention further provides therefore a process for biocompatibilising a surface which comprises:
(a) where the surface does not provide a polymeric substrate having reactive linking groups, activating the surface to provide a polymeric substrate having reactive linking groups; and
(b) grafting to the substrate, a compound of formula (I) as hereinbefore defined by reaction with reactive linking groups.

Preferences expressed above in connection with polyurethanes apply equally in relation to other polymer types.

The present invention will now be illustrated by the following Examples.

EXAMPLES

The polyurethanes used in Examples 1 to 10 are all commercially available. They have the following structures.

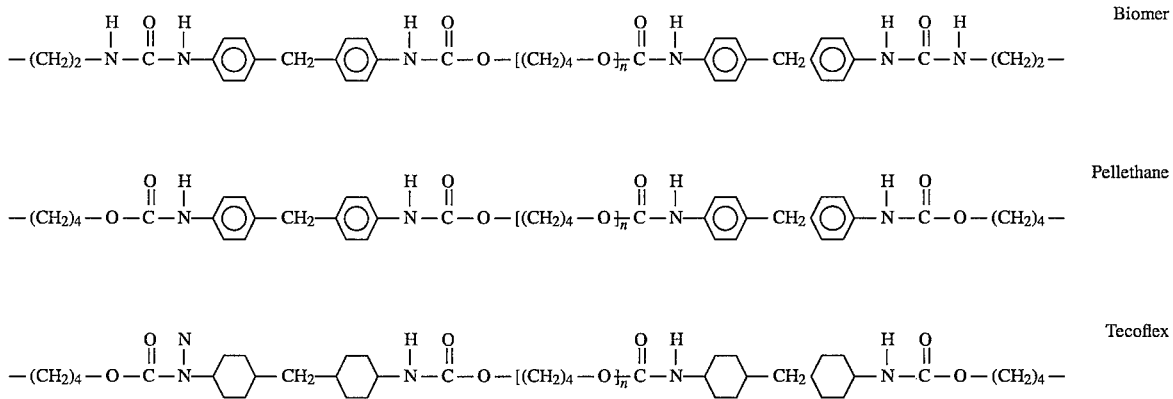

The production of prostheses from the polymers of the invention is accomplished generally via the procedures already practised by the polymer industry.

When a thermoplastic polymer, such as a polyurethane, is obtained it can be processed as a moulding material, e.g. by injection-moulding or extrusion. If a solid elastomer is obtained it can be used in the same processing employed with conventional rubber. The methods required for the processing of rubber vary according to the viscosity and reactivity of the intermediate alkylisocyanate.

Where the polymer of the present invention is to be used for coating, it will be dissolved in a suitable volatile solvent, for example a solvent that has been previously used in the production of the polymer, coated on to the article and the solvent allowed to evaporate.

The above-described compounds and techniques can be applied to the treatment of polymers, such as polyurethanes, in solution in inert solvents (such as dimethyl acetamide, dimethyl sulphoxide, THF or a mixture thereof) or at a polymer, such as a polyurethane surface. In addition, these compounds and techniques may be used to treat many other types of polymer, such as HEMA and HEMA/MA hydrogels, Cuprophan, Cellulose and Cellulose derivatives, Fibrinogen Absorption Assay Samples which were assayed for absorption of the protein fibrinogen were analysed by the following method.

The assay determines absorption of human fibrinogen at a surface. This protein is representative of protein which is typically adsorbed at a surface. The assay can be readily modified to determine the absorption of other proteins.

Discs (7 mm in diameter) of untreated material (as controls) and material treated with polymer as described below, were prepared and washed with phosphate buffered saline (PBS) for at least 10 minutes in the wells of microplates. The samples were incubated with human plasma (300 µl) for 10 minutes and then washed with PBS three times. Each of the test samples and each of the control samples were treated with human fibrinogen-specific antibody (300 µl) for 30 minutes and again washed with PBS three times. As a control for non-specific binding of antibody to the samples, each sample was also incubated with non-specific antibody (300 µl) for 30 minutes. A conjugate of horseradish peroxidase and a second antibody specific to the first antibody (300 µl) was added to both the test samples and the controls and incubated for 30 minutes before washing. Each of the test samples and the controls were transferred to new microplates and a solution of 2,2'-azino-bis(3-ethyl benzthiazoline-6-sulphonic acid) (ABTS) in phosphate-citrate buffer (300 μl, 0.6 mg/ml) added, the reaction was allowed to proceed for 10 minutes. At this time an aliquot of the mixture (200 μl) was removed and added to a solution of citric acid and sodium azide in distilled water (20 μl, 0.21 g/ml and 2 mg/ml respectively). The optical density of the solutions was measured using a Techgen automated plate reader at 650 nm using the ABTS solution as blank.

In an alternative procedure, rather than using ABTS, each of the samples was transferred to wells of new microplates and a solution of o-phenylene diamine (OPD) in phosphate-citrate buffer (300 μl, 0.4 mg/ml) added, and the reaction was allowed to proceed for 10 minutes. At this time an aliquot of the mixture (200 μl) was removed from each well and the optical density of the solutions was measured using a Techgen automated plate reader at 450 nm using the OPD solution as blank.

EXAMPLE 1

Coupling of phosphorylcholine ethanolamine to polyurethanes with di-isocyanate

Phosphorylcholine ethanolamine (PC—$NH_2$) was synthesised by the method of Durrani et al., (1986) Biomaterials, 7, 121. Alternatively, it may be obtained as described in WO-A-92/07858. PC—$NH_2$ has the following structure It has the following structure

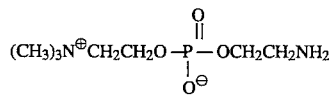

PC—$NH_2$ was reacted with excess hexamethylene diisocyanate in formamide solution (room temperature for 24 hours), according to the reaction:

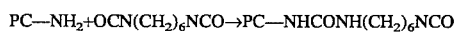

The resulting product was precipitated with dry ether and washed copiously with ether. It was coupled to polyurethane (the commercially available polymer, Biomer) in solution in a mixture of dimethylacetamide and dimethylsulphoxide (60° C. for 4 hours and then at 25° C. for 3 days). The resulting polymer was precipitated into water and washed extensively. The final adduct is thought to contain structures of the type produced according to the reaction:

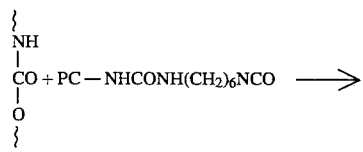

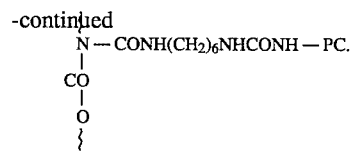

The product obtained had a phosphorus content of 0.59%.

EXAMPLE 2

Coupling of Glycerophosphorylcholine to Polyurethane with Cyanogen Bromide

Glycerophosphorylcholine, free from cadmium chloride was obtained commercially.

A modified polyurethane containing —$NH_2$ groups was obtained by first reacting trichloroacetylisocyanate with the commercially available polyurethane Biomer. Biomer sheet was immersed in hexane for 2 hours and then placed in a hexane solution of trichloroacetyl isocyanate (1 gm and 150 ml of hexane) for 3 hours. After this time the sheet was washed carefully with hexane and vacuum dried.

The reaction is represented as:

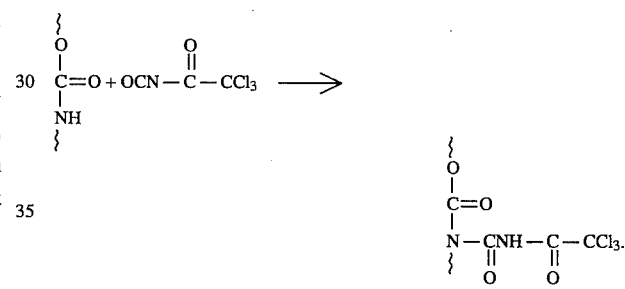

A sheet of trichloroisocyanated-Biomer was placed in the reaction vessel and solutions of a mixture (1.5 gm) of styrene and the amino monomer of formula (VA).

(m=3; 20% w/w amino monomer) dissolved in methanol (25 ml) and dirhenium carbonyl (0.08 gm) dissolved in ethylacetate (5 ml) were added. After degassing of the reaction mixture under vacuum, the vessel was sealed off.

Copolymerisation of the styrene and amino monomer of formula (VA) onto isocyanated polyurethane was carried out photochemically at room temperature (λ=365 nm) for 1 hour, then the grafting continued for 48 hours under a lamp (60 W) while the reaction vessel was rotating slowly. The polyurethane was washed off carefully with methanol followed by distilled water to remove any unreacted monomer and ungrafted copolymer and dried.

The graft formation is shown in the reaction. Triethylamine was mixed with cyanogen bromide in a solution of acetone and water (60% acetone, 40% water) then, glycerophosphorylcholine was added and allowed to stand 15 minutes at −15° C. Polyurethane modified to contain —NH₂ groups, (solid polymer) was then added and reaction continued overnight at room temperature. The product was washed extensively with water and dried. The phosphorus content of the resulting polymer was found to be 0.05%.

Coupling with cyanogen bromide is considered to proceed through the following scheme:

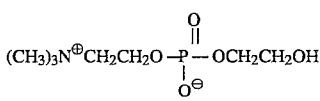

EPC (7.5 g, 0.033 mol) was dissolved in formamide (10 ml), then hexamethylene-diisocyanate (22.2 g, 0.123 mol) were

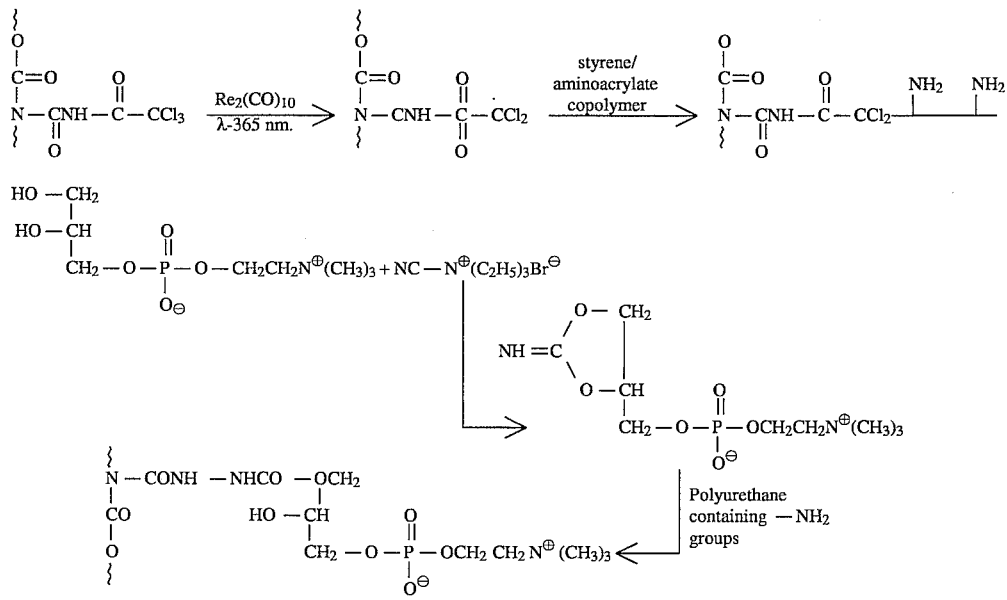

EXAMPLES 3–8

The method of Example 2 was repeated but using the commercially available polyurethane Tecoflex and a mixture of an amino acrylate of formula (IV) (n=3 or 6) and 2-hydroxyethylmethacrylate (HEMA) or hydroxypropylacrylamide (HPA). Details are given in the table below:

| Example | n | Comonomer Grafted with (IV) | % (w/w) of (IV) in copolymer mixture |
|---|---|---|---|
| 3 | 6 | HPA | 14.2 |
| 4 | 3 | HPA | 9.8 |
| 5 | 6 | HEMA | 4.9 |
| 6 | 6 | HEMA | 8.5 |
| 7 | 3 | HEMA | 3.5 |
| 8 | 6 | HEMA | 2.4 |

The phosphorus contents were determined for the products of Examples 3 and 5 and were found to be 0.06% and 0.08% respectively.

EXAMPLE 9

Coupling of Phosphorylcholine Ethylene Glycol to Polyurethane with Di-isocyanate Ethylene glycol phosphorylcholine (EPC) was synthesised as described by A. A. Durrani et al., Biomaterials (1986) 7, 121. Alternatively this may be obtained as described above.

added. The reaction was carried out at room temperature for 1.5 hours, then the commercially available polyurethane Tecoflex (11 gm) in DMAC solution (70 ml) was added. The reaction was continued for 24 hours at 40° C. and the whole reaction mixture precipitated into water. The polymer was filtered off and washed very carefully and vacuum dried.

The resulting polymer was found to have a phosphorus content of 0.22% and is thought to contain the following type of structure.

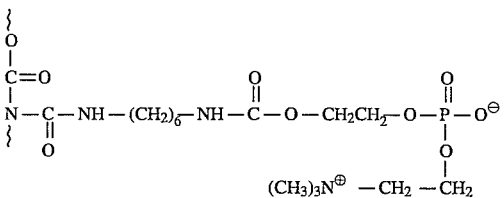

EXAMPLE 10

Photochemical Coupling of 2-Hydroxyethylmethacrylate Phosphorylcholine to Polyurethane The commercially available polyurethane, Pellethane, was functionalised by reaction with trichloroacetylisocyanate using the method described in Example 2.

Functionalised polyurethane was then reacted photochemically with 2(methacryloyloxy)-ethyl-2'(trimethylammonium)ethyl phosphate inner salt (HEMA-PC) (prepared using the reference Example which follows) (1.5 gm) in the presence of dirhenium decacarbonyl using the method described in Example 2.

The phosphate esters on both surfaces of the polyurethane sheet were detected by an Acid Molybdate Spray Reagent Kit (Sigma). This test was very positive on both surfaces of the grafted sheet of polyurethane.

The resulting product was shown by XPS analysis to have a phosphorus content of 0.63%. The reaction is shown schematically as follows:

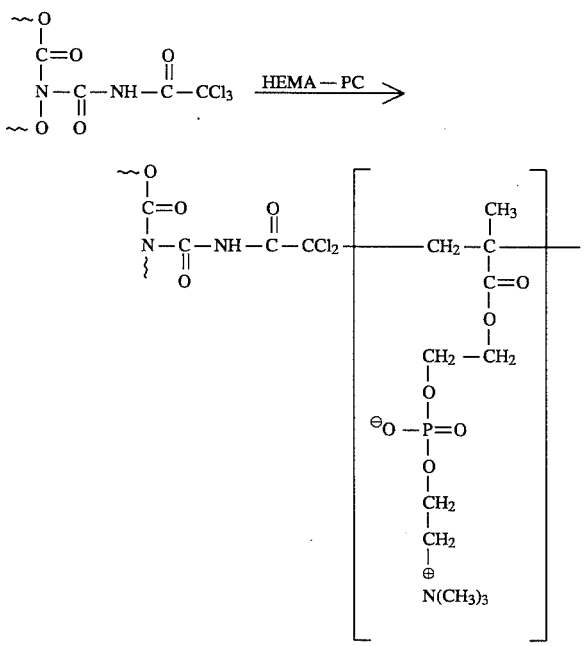

EXAMPLE 11

Platelet Adhesion Test, Using Sheep Blood

Films of polymers prepared according to Examples 1 to 8 and 10 were immersed in sheep platelet-rich-plasma for 4 hours at room temperature. They were then washed extensively with phosphate buffered saline, stained and photographed. The results were compared to photographs of equivalent polyurethane polymers which were untreated to add phosphorylcholine groups.

The photographs of the films treated according to the Examples showed significantly fewer platelets adhered to them compared to the corresponding untreated films, indicating increased haemocompatibility.

EXAMPLE 12

Platelet Adhesion Test, Using Human Blood

Blood was collected from three healthy adult volunteers using the double syringe method. The first 5 mls of blood were discarded. The blood was collected into tri-sodium citrate (32 g/l) in the proportion of 9 volumes to 1 volume citrate in plastic tubes. The samples were kept at room temperature on a spiral mixer until used. Pieces (22 mm$^2$) were cut from sheets of untreated polyurethane (Pellethane) and polyurethane treated according to Example 10. These were placed into Universal Containers (UC's). Whole citrated blood (3 mls) was then added to each of the tubes. The samples were incubated for 30 minutes on a spiral mixer at room temperature.

After incubation, samples were removed from the universal containers, washed in phosphate buffered saline (PBS) and then placed into extractant (2 mls). The extractant and samples were then mixed for 10 minutes.

The amount of ATP present in the extractant was estimated using the LKB ATP assay kit and a LKB 1251 luminometer, in accordance with manufacturer's instructions.

The number of platelets adhereing to the samples was estimated from a standard curve using known numbers of platelets. For the standard curve, platelet rich plasma (PRP) was prepared by centrifuging citrated venous samples at 150–200×g for 15 minutes at room temperature. Dilutions of PRP for each donor were prepared.

The number of platelets in each dilution was estimated using a Coulter counter. The amount of ATP associated with a known number of platelets was then calculated. These standard curves were then used to estimate the number of platelets adhering to surfaces.

The results obtained were as follows:

|  | Donor Plts × 10$^6$ | | | x̄ Plts | % |
|---|---|---|---|---|---|
| Sample | 1 | 2 | 3 | (× 10$^6$) | Reduction |
| Untreated Polyurethane | 7.28 | 8.44 | 5.19 | 6.97 | 0 |
| PC-bearing Polyurethane (Example 10) | 3.39 | 1.79 | 1.07 | 2.08 | 69.2 | plts: Platelets

EXAMPLE 13

Analysis of Platelet Adhesion Using Scanning Electron Microscopy

Samples of untreated polyurethane (Pellethane) and polyurethane (Pellethane) treated in accordance with Example 10 were prepared in accordance with Example 12. They were prepared for Scanning Electron Microscopy (SEM) by fixing in an aliquot of the following solution.

2 mls 25% glutaraldehyde 83 mls 0.15M PBS (pH 7.4)

15 mls saturated picric acid (Picric acid increases the preservation of lipid associated protein).

Before dehydration the samples were washed in PBS. The samples were then dehydrated using 70% methanol followed by absolute methanol. The samples were then transferred into 100% acetone and air dried. Finally samples were given a sputter coating with gold. (30 mAmps for 3 minutes).

Comparison of the micrographs obtained showed that the treated polyurethane had a significantly changed surface morphology from the untreated material. The platelet adhesion to the polyurethane surface was greatly reduced by the treatment and the majority of the surface was clear from platelet adhesion.

EXAMPLE 14

Measurement of Contact Angle

Samples of untreated polyurethane (Pellethane) and of polyurethane (Pellethane) treated in accordance with Example 10, were cleaned in water and their receding and advancing contact angles measured in water and in formamide. The results were as follow:

| Contact Angle Determinations | | | | | | | |
| --- | --- | --- | --- | --- | --- | --- | --- |
| Untreated polyurethane/Water | | | | | | | |
| Determination | 1 | 2 | 3 | 4 | 5 | 6 | x + S.D |
| Advancing | 102 | 99.6 | 98.3 | 104 | 101.6 | 100 | 101 ± 2 |
| Receding | 73.6 | 72.3 | 72.0 | 68.6 | 69.3 | 69 | 71 ± 2 |

| Treated Polyurethane accord Example 10/water | | | | | |
| --- | --- | --- | --- | --- | --- |
| Determination | 1 | 2 | 3 | 4 | x + S.D |
| Advancing | 79.5 | 86 | 84 | 81 | 83 ± 3 |
| Receding | 28 | 27.3 | 25 | 23 | 26 ± 2 |

| Untreated Polyurethane/Formamide | | | | | | | | | | |
| --- | --- | --- | --- | --- | --- | --- | --- | --- | --- | --- |
| Determination | 1 | 2 | 3 | 4 | 5 | 6 | 7 | 8 | 9 | x + S.D |
| Advancing | 69 | 69 | 70 | 73 | 71 | 70 | 73 | 69 | 68 | 70 ± 2 |
| Receding | 37 | 36 | 36 | 31 | 31 | 30 | 30 | 32 | 33 | 33 ± 3 |

| Polyurethane Treated according to Example 10/Formamide | | | | | | | |
| --- | --- | --- | --- | --- | --- | --- | --- |
| Determination | 1 | 2 | 3 | 4 | 5 | 6 | x + S.D |
| Advancing | 70 | 69 | 67 | 72 | 69 | 64 | 69 ± 3 |
| Receding | 26 | 26 | 25 | 27 | 27 | 27 | 26 ± 3 |

A notable difference was observed between the treated and untreated samples. In particular in the receding contact angles, which more closely approximate to the static contact angle than the advancing contact angles, a significant decrease is observed in the treated samples. This indicates an increase in wettability upon treatment of the polyurethane in accordance with the present invention.

EXAMPLE 15

Grafting of HEMA PC onto HEMA Membrane a) Preparation of HEMA membrane

A mixture of distilled HEMA (29.70 g), ethylene glycol dimethacrylate (0.30 g) and benzoyl peroxide (0.03 g) was degassed by bubbling nitrogen through for 10 minutes. The clear solution was then transferred to a mould constructed from 2 melamine lined glass sheets separated by a gasket formed from a length of silicone rubber tubing (o.d. 2.5 mm, i.d. 1 mm). The filled mould was then placed in an oven (at 65°–70° C. for 18 hours). The mould was then cooled to room temperature, opened, and the gel removed. The gel was then placed in distilled water, to hydrate and remove unreacted monomer. After 24 hours the water was replaced, and the gels stored in water until required.

b) Grafting with HEMA PC A sheet of the above HEMA gel (ca. 20.3 g wet weight) was placed in a reaction vessel made from two sheets of glass separated by a gasket formed from a silicone rubber tube (o.d. 5 mm; so as to allow the grafting solution to reach both sides of the membrane. This procedure was used to reduce the amount of grafting solution required, yet hold the gel flat). The apparatus was then flushed with nitrogen.

A solution of HEMA PC (6.04 g) in water (to give 50 ml of solution) was then prepared, and deoxygenated by bubbling nitrogen through for 10 minutes. Ceric ammonium nitrate (0.27 g) was then added, to give a turbid solution of HEMA PC (0.204M), and ceric ammonium nitrate ($5 \times 10^{-3}$M). The solution was then poured into the reaction vessel, so as to totally immerse the gel. A nitrogen bleed was fitted to bubble nitrogen through the solution, and the charged apparatus was then placed in an oven held at 50° C. for 2.5 hours.

The now viscous solution was poured out of the apparatus, and the grafted gel removed. It was washed for 30 minutes under running tap water, then stirred gently in 500 ml of distilled water for 15 minutes. The water was changed, and the gel gently stirred for a further 15 minutes. This was repeated a further 2 times, then the gel was left overnight in fresh distilled water. The surface of the gel was noticeably more hydrophilic, and a small section was tested with acid molybdate reagent to give an intense blue colouration. FTIR(ATR) showed some differences between the grafted and ungrafted material, although, there was no obviously assignable difference.

EXAMPLE 16

Grafting of HEMA PC onto HEMA: methacrylic acid contact lenses

HEMA: methacrylic acid contact lenses were placed in distilled water (300 ml) and stirred gently for 10 minutes. The lenses were then placed in individual vials, along with ca 5 ml of fresh distilled water.

A solution of HEMA PC (4.72 g) in distilled water (75 ml) was then prepared, and deoxygenated by bubbling nitrogen through for 10 minutes. Ceric ammonium nitrate (0.2192 g) in water (5 ml) was then added, to give a slightly turbid solution of HEMA PC (0.2M) and ceric ammonium nitrate ($5 \times 10^{-3}$M). The water was removed from the lenses with the aid of a pasteur pipette, and ca 2 ml of the HEMA PC/ceric nitrate solution added to each lens. The vials were then flushed with nitrogen, sealed, and placed in a thermostatted water bath held at 50° C. for 4.5 hours. After this time, the grafting solution had increased in viscosity slightly. The slightly cloudy lenses were removed, and placed in a beaker containing 1 l of distilled water and gently stirred for 10 minutes. The water was then replaced, and the procedure repeated twice. Two lenses were taken and tested with acid molybdate reagent. Both gave an intense blue colouration indicating the presence of phosphate. On sectioning a lens before staining with acid molybdate reagent, the staining was observed to occur on a thin surface layer, which had been exposed to the grafting solution. No staining was observed in the freshly exposed portion of the lens which had not been in contact with the HEMA PC/ceric ammonium nitrate solution.

The lenses were incubated overnight in 500 ml of phosphate buffered saline (PBS). The slightly cloudy appearance observable initially in the lenses was removed, to leave clear lenses. The PBS was then removed, and replaced with distilled water (700 ml). (The PBS was added to help in the removal of any ceric residues complexed to the grafted phosphate moieties). The lenses were then gently stirred for 10 minutes, and the water replaced with borate buffered saline. The lenses were then transferred to individual vials containing borate buffered saline. The equilibrium water content of the lenses was measured, and was found to show an increase of approximately 1% over the untreated lenses. The absorption of lysozyme by the treated lenses was found to be comparable with that observed for untreated controls. Surface analysis confirmed the presence of nitrogen and phosphorus on the surface of a dehydrated, treated lens.

EXAMPLE 17

Grafting of HEMA PC onto Cuprophan

A sample of Cuprophan was placed in distilled water for 1 hour, changing the water on several occasions to remove the glycerol plasticiser. The sample was then placed in a solution of HEMA PC (0.885 g) in distilled water (4.5 ml). The solution was then deoxygenated by bubbling nitrogen through for 10 minutes. The resulting solution was then treated with a solution of ceric ammonium nitrate (0.0275 g) in distilled water (0.5 ml). Deoxygenation was continued for a further 5 minutes. The reaction vessel was then sealed, and placed on a spiramix (4.25 hours at room temperature). After this time the viscosity of the solution had increased markedly. The cuprophan sample was removed, and washed extensively with distilled water. The samples were then soaked in distilled water, which was replaced after 5, 10, 30, 60 and 90 minutes then left overnight.

The treated cuprophan showed a very strong positive test with acid molybdate spray reagent, indicating the presence of phosphate in the sample. Control samples (ie untreated, treated with HEMA PC alone, and treated with ceric ammonium nitrate alone under the same reaction conditions and washing procedure) did not give a positive test.

The HEMA PC grafted cuprophan showed a slight increase in platelet adhesion and protein adsorption. This was probably due to the fact that native cuprophan itself has a very low tendency to absorb platelets etc. However, the grafted cuprophan showed a 90% reduction in complement activation, as shown by radioimmunoassay, ($C_{3a}$, kit, ex Amersham International).

EXAMPLE 18

Grafting of HEMA PC onto cellulose acetate

A section of cellulose acetate filtration membrane (pore size 2 microns, 100% acylated: ex Sartorius) was cut into two strips, (total weight 0.4103 g), and placed into 20 ml polypropylene centrifuge tubes. A solution of HEMA PC (2.655 g) in distilled water (29.5 ml) was prepared and degassed by bubbling argon through the solution for 10 minutes. The solution was then treated with a solution of ceric ammonium nitrate (0.0815 g) in water (1 ml), and the deoxygenation continued for a further 5 minutes. The solution was then divided into two portions, and added to the centrifuge tubes containing the cellulose acetate. The tubes were flushed with argon, sealed, then placed on a spiraxmix and gently agitated for 5 hours at room temperature. The samples were then removed from the now viscous solution, and washed well with water. The samples were then placed in distilled water (20 ml), and agitated on the spiramix (1 hour). The water was changed, and the procedure repeated. Initially the water was changed every hour for four hours. The samples were then incubated in distilled water for 2 days at room temperature. Finally, the samples were dried under reduced pressure at 50° C. After drying the total weight of the grafted samples was found to be 0.4105 g (0.04% by weight increase). The presence of phosphate on the surface was demonstrated by staining with acid molybdate reagent.

The flux rate of the treated cellulose acetate membrane was determined using distilled water, and was found to be comparable with that of the untreated material (an average of a 2.73% reduction in flux rate was determined). The absorption of fibrinogen onto the treated membrane showed a 17% reduction on that observed for an untreated sample.

EXAMPLE 19

Grafting of HEMA PC onto polyvinyldifluoride (PVDF)

A circular sample of hydrophobic polyvinyldifluoride (PVDF) filtration membrane (pore size 2 microns) was cut (9 cm diameter). The membrane was then placed in the chamber of a Polaron Bio-Rad plasma barrel etcher and subjected to an oxygen plasma of 10 Watts power, at a pressure of 0.2 mbar for 5 minutes. The now hydrophilic PVDF membrane was removed from the chamber, and placed in a solution of HEMA PC and ceric ammonium nitrate (concentration 0.15M and $5\times10^{-3}$M respectively). The solution was deoxygenated for 10 minutes, then the vessel was sealed. The mixture was gently agitated on a spiramix (room temperature, 1 hour). The PVDF sample water-soluble then removed, and washed well with distilled water. Finally, the sample was left overnight in distilled water, then air dried. Staining with acid molybdate reagent revealed the presence of phosphate on the treated membrane. The flux rate of the treated membrane was determined, and was found to show a 20% reduction over that observed for an untreated control membrane. Fibrinogen absorption reduction was found to be of the order of 30%, as determined by an immunoabsorbant assay. Surface analysis, using XPS revealed the presence of 4% phosphorus on the surface of the membrane.

Comparative Example 1

Absorption of HEMA PC on nitrocellulose

The nitrocellulose used for this study (and for Example 20) was in the form of a coating laid down from a methanol/water slurry onto a mylar backing sheet.

A small section of nitrocellulose was cut and used as a the support. A dilute solution of HEMA PC in water was applied with a capillary tube, and the spot was dried with compressed air. The nitrocellulose plate was placed in distilled water and the chromatogram run. When the solvent front had reached the top of the plate, the plate was removed, dried with compressed air, then sprayed with Dragendorff's reagent to reveal the position of the HEMA PC. It was found that the HEMA PC had an Rf of 1. This result indicates that HEMA PC monomer would wash off nitrocellulose very easily with water.

EXAMPLE 20

Grafting of HEMA PC onto nitrocellulose
a) With Ceric ammonium nitrate.

A section of nitrocellulose on mylar sheet (14.2203 g) was placed in a reaction vessel constructed from 2 sheets of glass separated by a gasket of silicone rubber. This type of vessel was used to reduce the amount of solution required.

A solution (0.3M) of HEMA PC (13.27 g) in water (150 ml) was deoxygenated by bubbling nitrogen through for 15 minutes. A solution of ceric ammonium nitrate (0.411 g) in water (1 ml) was then added to the HEMA PC solution to give a slightly turbid, pale yellow solution (0.3M HEMA PC; $5\times10^{-3}$M Ceric ammonium nitrate). Nitrogen was bubbled through for a further 5 minutes. The solution was then transferred to the vessel containing the nitrocellulose sample, ensuring the sample was completely immersed. Nitrogen was blown over the solution to restrict the ingress of oxygen. The nitrocellulose was left in the solution at room temperature for 3 hours, during which time the viscosity of the solution increased significantly.

The vessel was then opened, and the nitrocellulose removed, and washed extensively in distilled water for 2 hours, changing the water regularly. (The mylar backing sheet was observed to be extremely slippery, even after prolonged washing). The nitrocellulose was then dried at room temperature in a laminar flow hood for 2 hours. After drying the sample was found to weigh 14.1167 g, ie a weight reduction, (possibly indicating the leaching out of low molecular weight material from the nitrocellulose).

The presence of HEMA PC on the surface was indicated by a positive test with Dragendorff's reagent and acid molybdate spray reagent. However, with the acid molybdate reagent, spraying onto even ungrafted nitrocellulose will give an immediate blue colouration. (This may be overcome by placing the test samples into a small quantity of undiluted reagent). The presence of grafted material was also indicated by the uptake of iodine vapour, methylene blue solution, and eosin yellow solution, all of which are absorbed much more strongly on the grafted material than on a control sample.

The sample was then soaked for 1 hour in a 3% w/v solution of disodium orthophosphate (to remove bound ceric ions), followed by 1 hour in distilled water. The sample was then dried in a laminar flow hood for 1 hour, then overnight under reduced pressure. The grafted nitrocellulose showed a 91% reduction in albumin adsorption, as compared to an untreated sample.

The sample of nitrocellulose was removed from the mylar backing by dissolution in methanol (10 ml). The solution was filtered to remove a small quantity of gelatenous material and the clear filtrate added dropwise to a rapidly stirred quantity of distilled water (200 ml) to precipitate the grafted nitrocellulose which was then recovered by filtration. The recovered solid was redissolved in methanol (10 ml) and reprecipitated into water (200 ml). The recovered solid was then dried under vacuum and analysed for phosphorus. Microanalysis showed the phosphorus content of the treated nitrocullulose to be 0.16%.

b) With azobiscyanovaleric acid (i) A solution of HEMA PC (2.21 g), ethylene glycol bismethacrylate (0.11 g, 4.9% w/w) and azobiscyanovaleric acid (0.01 g) was dissolved in a mixture of distilled water (22 ml) and methanol (8 ml; ie 26% v/v methanol; this solvent mixture was shown not to dissolve nitrocellulose) to give a clear solution (the methanol was added to ensure dissolution of the ethylene glycol bismethacrylate). This solution was then poured carefully over the nitrocellulose sample (10.3316 g), to totally wet the nitrocellulose. Excess solution was then carefully blotted off the surface with a filter paper, and the nitrocellulose allowed to air dry for 30 minutes. The nitrocellulose sheet was then placed in a glass tank, which was flushed with nitrogen for 30 minutes, then sealed. The tank was then held at 60° C. for 22 hours. The nitrocellulose was then removed, and placed in distilled water and soaked for 2 hours. The hydration appeared to be uneven. The nitrocellulose was removed from the distilled water, and dried for 3 hours at room temperature in a laminar flow hood. The weight of the sample after drying was 10.3695 g (an increase of 0.0379 g). The sample gave positive tests for grafted HEMA PC as indicated in a) above.

(ii) The above procedure was repeated, using a solution of HEMA PC (2.95 g), ethylene glycol bismethacrylate (0.16 g, 5.4% w/w), and azobiscyanovaleric acid (0.01 g) in water (14 ml) and methanol (6 ml). (HEMA PC concentration 0.5M). The solution was applied to the nitrocellulose sample (12.1060 g) and left to soak in for 5 minutes before the surplus solution was carefully blotted off with a filter paper. The sample was then dried in a laminar flow hood for 30 minutes, then placed in a vessel constructed from two glass plates separated by a silicone rubber gasket. The apparatus was purged with nitrogen, sealed, then held at 60° C. for 16 hours.

The nitrocellulose was removed, and washed well with distilled water, then placed in distilled water for 1 hour. The sample was then washed with a 25% methanol/75% water mixture to remove any unreacted ethylene glycol dimethacrylate, and finally rinsed with distilled water. The sample was dried in a laminar flow hood and weighed (12.1706 g; 0.0646 g increase). The sample gave positive tests (ie staining with acid molybdate reagent and Dragendorff's reagent) for the presence of grafted HEMA PC.

EXAMPLE 21

Grafting of HEMA PC onto polyamide

The polyamide samples used for these studies were blood clot filtration screens comprising a nylon 6,6 mesh fitted with polypropylene end caps and support ribs.

The polyamide screens were first cleaned of any surface contaminants by soaking for 1 hour at 60° C. in a solution of sodium dodecyl sulphate (1.5 g) and sodium carbonate (1 g) in distilled water (1000 ml). On removal, the screens were washed extensively with distilled water, then dried in vacuum.

(i) 4 prewashed screens, (total weight 4.5103 g) were stirred for 10 minutes in a solution of commercial sodium hypochlorite, which had been acidified to pH 5 with glacial acetic acid. The screens were then removed, washed well with distilled water, then dried overnight under reduced pressure at 50° C. The weight of the screens was 4.5243 g (is 0.014 g increase; 0.31%). The screens were then placed in a glass tube fitted with a cone and sealing constriction.

A solution of HEMA PC (13.00 g) in methanol (60 ml) was treated with a solution of molybdenum hexacarbonyl (0.015 g) in ethyl acetate (ca. 1 ml) to give a clear colourless solution, which was added to the vessel containing the screens. The solution was degassed on a vacuum line at $5 \times 10^5$ mbar, by the freeze/pump/thaw method, and the reaction vessel sealed under vacuum. On thawing, the tube was held at 80° C. for ca. 100 minutes. After this time, the solution had become yellow (molybdenum pentacarbonyl chloride), and viscous, (indicating homopolymerisation had occurred). The tube was opened, and the screens removed, and washed well with methanol, followed by distilled water. To destroy residual N-chloro functionalities, the screens were placed in a solution of potassium iodide (1%), which produced an immediate deep brown colouration (iodine) on the surface of the screens. The screens were left in the KI solution for 5 minutes, removed and placed in a solution of sodium thiosulphate (0.1M). The screens were left stirring overnight, which resulted in most of the brown iodine stain being removed. The screens were then left soaking in distilled water for several days, the water being changed frequently. On drying in vacuum at 50° C., the weight of the screens was found to be 4.6163 g (2.35% weight increase). The screens were extremely hydrophilic, and the mesh surface was extremely slippery. One screen was tested for dye uptake. Methylene blue was readily absorbed onto the mesh, but very little was absorbed onto the polypropylene supports.

The treated polyamide screen (after removal from the polypropylene components) was then tested for platelet adsorption, using an ATP assay. A 20% reduction in platelet adsorption over that observed for untreated control samples was observed.

(ii) 4 prewashed screens stirred for 5 minutes in a solution of commercial sodium hypochlorite, which had been acidified to pH 4.5 with glacial acetic acid. The screens were then removed, washed well with distilled water, then dried overnight under reduced pressure at 50° C.

The weight of the screens was 4.4787 g.

A solution of HEMA PC (10.02 g) in methanol (80 ml) was treated with a solution of molybdenum hexacarbonyl (0.13 g) in ethyl acetate (ca. 10 ml) to give a clear colourless solution, which was then diluted to 100 ml with methanol. The solution was placed in a 100 ml thick walled tissue culture bottle and deoxygenated by bubbling nitrogen through for 20 minutes. The vessel was sealed and held at 80° C. for 100 minutes. After this time, the solution had become yellow (molybdenum pentacarbonyl chloride), but there was no real increase in viscosity (indicating homopolymerisation had not occurred this time). The vessel was opened, and the screens removed, and washed well with methanol, followed by distilled water. To destroy residual N-chloro functionalities, the screens were placed in a solution of potassium iodide (1% w/v) and sodium thiosulphate (2% w/v). This produced only a faint brown colouration on the surface of the screens. The screens were left in the KI solution for 5 minutes, removed and placed in a solution of sodium thiosulphate. The screens were left stirring overnight, which resulted in most of the brown iodine stain being removed. The screens were then left soaking in distilled water for several days, the water being changed frequently. On drying in vacuum at 50° C., the weight of the screens was found to be 4.4959 g. The screens were hydrophilic, and the mesh surface slippery. One screen was tested for dye uptake. Methylene blue was absorbed onto the mesh, albeit faintly, but none was absorbed onto the supports. When tested for platelet adsorption (ATP assay), the nylon 6,6 mesh gave a reduction of 59% as compared to untreated samples.

EXAMPLE 22

HEMA PC grafting onto pre-oxidised polyamide

A solution of peracetic acid was prepared from glacial acetic acid (30 ml) and 30% hydrogen peroxide (10 ml) along with a catalytic amount of conc. sulphuric acid. The peracid solution was placed in a pyrex vessel, along with 2 polyamide screens of the type used in Example 21 screens (total weight 2.1966 g). The vessel was then placed in a Rayonet photolyser, fitted with both 254 nm and 360 nm tubes, and irradiated at ambient temperature for 6 hours. The screens were then removed, and washed well with distilled water, and finally stirred with distilled water overnight. The screens were then placed in a deoxygenated solution of HEMA PC (1.77 g) and ceric ammonium nitrate (0.059 g) in water (20 ml of solution; 0.3M HEMA PC, $5 \times 10^{-3}$M ceric ammonium nitrate). The screens were removed after ca. 4 hours, during which time the viscosity increased markedly. The screens were washed well with distilled water, stood for two days in distilled water, then finally dried under reduced pressure (2.2042 g; 0.0076 g or 0.35% weight increase). The mesh was found to be more hydrophilic, and showed dye uptake indicative of the surface being grafted with a hydrophilic polymer. When tested for platelet adhesion, using an ATP assay, a reduction of 82% relative to an untreated control was observed.

EXAMPLE 23

Grafting of HEMA PC onto polyimide

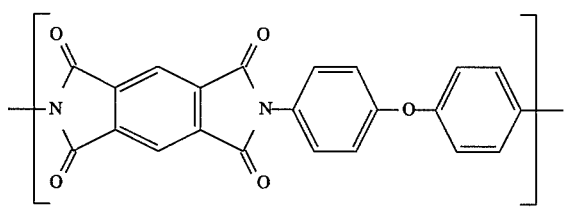

Polyimide repeating unit

Samples of a film of the polyimide were cut into squares (7×7 mm), then cleaned by sonication in a solution of SDS (0.15%) and sodium carbonate (0.1%) in distilled water. The SDS was then removed and the samples rinsed with distilled water. The polyimide were then air dried. After cleaning, the samples were observed to be hydrophobic. The samples were then placed in the chamber of a Polaron Bio-Rad plasma barrel etcher, and subjected to an oxygen plasma generated at 0.2 mbar, using a forward power of 100 watts. The samples were subjected to the plasma discharge for 10 minutes on each side. Following the plasma treatment, the polyimide samples were found to be extremely hydrophilic.

A solution was prepared from 3-(trimethoxysilyl)propyl methacyrlate (1 ml), isopropanol (2 ml), glacial acetic acid (3 drops) and distilled water (30 ml). The initially two phase mixture was shaken at room temperature for approximately 10 minutes, after which time a homogenous clear solution was produced. The polyimide samples were then added, and the mixture gently agitated overnight at room temperature. The supernatant solution (now containing some oily droplets) was then decanted off. The samples were then washed well with water (5×30 ml) followed by ethanol (2×30 ml), then air dried. The samples were now found to be extremely hydrophobic.

HEMA PC grafting
Method a

The methacryloylated polyimide samples were added to a solution of HEMA PC (1.46 g) in distilled water (5 ml). Sodium thiosulphate (0.05 g) was added to the solution which was then deoxygenated by bubbling nitrogen through it for 10 minutes. Ammonium persulphate (0.05 g) was then added and the deoxygenation continued for a further 5 minutes. The reaction vessel was then closed, and stood at room temperature overnight. The solution, which was observed to have increased in viscosity, was then decanted off. The grafted samples were then washed extensively in distilled water for several hours, then air dried. The samples were found to be extremely hydrophilic, but staining with acid molybdate reagent was inconclusive. Surface analysis (XPS) of the treated samples however revealed the presence of phosphorus.

Samples showed a 28% reduction in absorption of fibrinogen and a 94% reduction in platelet activation compared to untreated samples.

Method b

The methacryloylated polyimide samples were added to a solution of HEMA (5 ml) in ethanol (10 ml), to which was added AIBN (0.01 g). The solution was deoxygenated by bubbling nitrogen through it for 15 minutes. The reaction vessel was sealed and placed in a water bath at 60° C. The reaction vessel was shaken at regular intervals. After 6 hours the solution was observed to have increased in viscosity markedly. The viscous supernatant was decanted off the polyimide samples which were then washed with ethanol (3×30 ml), methanol (3×30 ml) and left overnight at room temperature in methanol (100 ml). The methanol washed samples were then removed, washed with water (3×30 ml) and finally air dried. The HEMA grafted samples were observed to be hydrophilic.

The HEMA grafted samples were then placed in a solution of HEMA PC (0.44 g) in distilled water (4.5 ml), and deoxygenated by bubbling nitrogen through the solution for 10 minutes. A solution of ceric ammonium nitrate (0.014 g) in distilled water (0.5 ml) was added. Deoxygenation was continued for a further 5 minutes. The reaction vessel was closed, and placed on a spiramix (room temperature for four hours). The resulting viscous supernatant solution was removed, and the treated samples washed well with water (5×20 ml, agitating for 10 minutes before each change of water). The samples were then left overnight in distilled water (20 ml), being gently agitated on a spiramix. The samples were then air dried. The extremely hydrophilic polyimide samples gave an inconclusive test for phosphate with acid molybdate reagent, but the presence of phosphorus on the surface was shown by surface analysis (XPS).

The samples showed a 65% reduction in fibrinogen absorption and 92% reduction in platelet activation relative to untreated material. This may be compared to a reduction of 27% in fibrinogen absorption and 99% in platelet activation for control material treated with a HEMA layer only.

EXAMPLE 24

Grafting of HEMA-PC onto Silicone Rubber

By analogy with Example 23, samples of silicone rubber film were cut into squares (7×7 mm), then cleaned by sonication in a solution of SDS (0.15%) and sodium carbonate (0.1%) in distilled water. The SDS was then removed, and the samples rinsed with distilled water. The silicone rubber samples were then air dried. The samples were then placed in the chamber of a Polaron Bio-Rad plasma barrel etcher, and subjected to an oxygen plasma generated at 0.2 mbar, using a forward power of 100 watts. The samples were subjected to the plasma discharge for 10 minutes on each side. Following the plasma treatment, the silicone rubber samples were found to be extremely hydrophilic. The samples were then placed immediately into a solution prepared from 3-(trimethoxysilyl)propyl methacrylate (1 ml), isopropanol (2 ml), glacial acetic acid (3 drops) and distilled water (30 ml). (The initially two phase mixture was shaken at room temperature for approximately 10 minutes, after which time homogenous clear solution was produced). The mixture was gently agitated overnight at room temperature. The supernatant solution (now containing some oily droplets) was then decanted off. The samples were then washed well with water (5×30 ml) followed by ethanol (2×30 ml), then air dried. The samples were now found to be extremely hydrophobic.

HEMA PC grafting
Method a

The methacryloylated silicone rubber samples were added to a solution of HEMA PC (1.46 g) in distilled water (5 ml). Sodium thiosulphate (0.05 g) was added to the solution which was then deoxygenated by bubbling nitrogen through it for 10 minutes. Ammonium persulphate (0.05 g) was then added and the deoxygenation continued for a further 5 minutes. The reaction vessel was closed, and stood at room temperature overnight. The solution, which was observed to have increased in viscosity, was then decanted off. The grafted silicone rubber samples were then washed extensively in distilled water for several hours, then air dried. The samples were found to be extremely hydrophilic, but staining with acid molybdate reagent was inconclusive. Surface analysis (XPS) of the treated silicone rubber samples however revealed the presence of phosphorous. Samples showed a 28% reduction in absorption of fibrinogen and a 76% reduction in platelet activation compared to untreated material.

Method b

The methacryloylated silicone rubber samples were added to solution of HEMA (5 ml) in ethanol (10 ml), to which was added AIBN (0.01 g). The solution was deoxygenated by bubbling nitrogen through it for 15 minutes. The reaction vessel was sealed and placed in a water bath held at 60° C. The solution was shaken at regular intervals. After 6 hours the solution was observed to have increased in viscosity markedly. The viscous supernatant solution was decanted off the silicone rubber samples, which were then washed with ethanol (3×30 ml), methanol (3×30 ml), and left overnight at room temperature in methanol (100 ml). The methanol washed samples were then removed, washed with water (3×30 ml) and finally air dried. The HEMA grafted silicone rubber samples were observed to be hydrophilic.

The HEMA grafted silicone rubber samples were then placed in a solution of HEMA PC (0.44 g) in distilled water (4.5 ml), and deoxygenated by bubbling nitrogen through the solution for 10 minutes. A solution of ceric ammonium nitrate (0.014 g) in distilled water (0.5 ml) was added. Deoxygeneation was continued for a further 5 minutes. The reaction vessel was closed, and placed on a spiramix at room temperature for four hours. The resulting viscous supernatant solution was removed, and the treated samples washed well with water (5×20 ml, agitating for 10 minutes before each change of water). The samples were then left overnight in distilled water (20 ml), being gently agitated on a spiramix. The samples were then air dried. The extremely hydrophilic silicone rubber samples gave an inconclusive test for phosphate with acid molybdate reagent, but the presence of phosphorus on the surface was shown by surface analysis (XPS).

Samples showed a 62% reduction in fibrinogen absorption and 60% reduction in platelet activation relative to untreated material. This may be compared to a 25% reduction in fibrinogen absorption for control material treated with a layer of HEMA only.

EXAMPLE 25

Grafting Of HEMA PC onto Stainless Steel

By analogy with Example 23 samples of stainless steel film were cut into squares (6×6 mm), then cleaned by sonication in a solution of SDS (0.15%) and sodium carbonate 0.1% in distilled water. The SDS was then removed, and the samples rinsed with distilled water. The stainless steel samples were then air dried. The samples were then placed in the chamber of a Polaron Bio-Rad plasma barrel etcher, and subjected to an oxygen plasma generated at 0.2 mbar, using a forward power of 100 watts. The samples were subjected to the plasma discharge for 10 minutes on each side. Following the plasma treatment, the stainless steel samples were found to be extremely hydrophilic.

A solution was prepared form 3-(trimethoxysilyl)propyl methacrylate (1 ml), isopropanol (2 ml), glacial acetic acid (3 drops) and distilled water (30 ml). The initially two phase mixture was shaken at room temperature for approximately 10 minutes, after which time a homogenous clear solution was produced. The stainless steel samples were then added, and the mixture gently agitated overnight at room temperature. The supernatant solution (now containing some oily droplets) was then decanted off. The samples were then washed well with water (5×30 ml) followed by ethanol (2×30 ml), then air dried. The samples were now found to be extremely hydrophobic.

HEMA PC grafting

Method a

The methacryloylated stainless steel samples were added to a solution of HEMA PC (1.46 g) in distilled water (5 ml). Sodium thiosulphate (0.05 g) was added to the solution which was then deoxygenated by bubbling nitrogen through it for 10 minutes. Ammonium persulphate (0.05 g) was then added and the deoxygenation continued for a further 5 minutes. The reaction vessel was then closed, and stood at room temperature overnight. The solution, which was observed to have increased in viscosity, was then decanted off. The grafted stainless steel samples were then washed extensively in distilled water for several hours, then air dried. The samples were found to be extremely hydrophilic, but staining with acid molybdate reagent was inconclusive. Surface analysis (XPS) of the treated stainless steel samples however revealed the presence of phosphorous. Samples showed a 57% reduction in fibrinogen absorption and an 83% reduction in platelet activation compared to untreated material.

Method b

The methacryloylated stainless steel samples were added to a solution of HEMA (5 ml) in ethanol (10 ml), to which was added AIBN (0.01 g). The solution was deoxygenated by bubbling nitrogen through it for 15 minutes. The reaction vessel was then sealed, placed in a water bath held at 60° C. The solution was shaken at regular intervals. After 6 hours the solution was observed to have increased in viscosity markedly. The viscous supernatant solution was decanted off the stainless steel samples, which were then washed with ethanol (3×30 ml), then with methanol (3×30 ml), finally left overnight at room temperature in methanol (100 ml). The methanol washed samples were then removed, washed with water (3×30 ml) and finally air dried. The HEMA grafted stainless steel samples were observed to be hydrophilic.

The HEMA grafted stainless steel samples were then placed in a solution of HEMA PC (0.44 g) in distilled water (4.5 ml), and deoxygenated by bubbling through the solution for 10 minutes. A solution of ceric ammonium nitrate (0.014 g) in distilled water (0.5 ml) was added. Deoxygenation was continued for a further 5 minutes. The reaction vessel was closed, and placed on a spiramix at room temperature for four hours. The resulting viscous supernatant solution was removed, and the treated samples washed well with water (5×20 ml, agitating for 10 minutes before each change of water). The samples were then left overnight in distilled water (20 ml), being gently agitated on a spiramix. The samples were then air dried. The extremely hydrophilic stainless steel samples gave an inconclusive test for phosphate with acid molybdate reagent, but the presence of phosphorus on the surface was shown by surface analysis (XPS).

Samples showed a 68% reduction in fibrinogen absorption and 58% reduction in platelet activation relative to untreated material. This may be compared to a reduction of 70% in fibrinogen absorption and 80% in platelet activation for a control sample coated with the HEMA layer only.

Further examples of grafting HEHA-PC to stainless steel are given in Examples 28, 29 and 31–35.

EXAMPLE 26

Grafting of HEMA-PC onto Polypropylene

A sample of polypropylene film (10 cm×10 cm) was activated by exposure to ozone for 15 minutes at room temperature. (The ozone was generated in a conventional silent discharge generator).

The activated film was then placed in a deoxygenated solution of HEMA PC (0.3M) and ceric ammonium nitrate ($4.5\times10^{-3}$M) in water. The film was left immersed in the solution for 5 hours at room temperature. On removal, the film was washed extensively with distilled water. The film was observed to be very hydrophilic, and gave a positive test for phosphate using acid molybdate reagent. The treated polypropylene was found to give a 76% reduction in fibrinogen adsorption as compared to an untreated sample.

EXAMPLE 27

Grafting of HEMA-PC to glass ($Re_2(CO)_{10}$ initiation)

A glass sample was cleaned and etched in order to increase the available functionality on the surface and then placed in a solution of polyethylene imine silane (2%) for 2 hours. The glass was then dried in a desiccator overnight. The imine was then chlorinated by immersion in water:sodium perchlorate 2:1 previously acidified with acetic acid to generate chlorine for 10 minutes.

The sample was removed from the chlorination reaction medium and placed in a degassed HEMA-PC solution (0.3M) containing $Re_2(CO)_{10}$ ($5\times10^{-4}$M). The solution was irradiated with U.V. light for half an hour and then left overnight under a 60 W lamp.

The sample was washed and dried.

The sample was assayed for adsorption of Horse-radish peroxidase immunoglobulin G. conjugate by a procedure analogous to that used for assay of fibrinogen absorption and showed a reduction of 89% compared to the untreated sample.

EXAMPLE 28

Grafting of HEMA-PC to steel ($Re_2(CO)_{10}$ initiation)

A stainless steel sample was cleaned as in Example 25. The sample was treated with polyethylene imine and chlorinated by a procedure analogous to Example 27. HEMA-PC was then grafted onto the sample, by a procedure analogous to that of Example 27. The sample gave a 68% reduction in fibrinogen adsorption relative to an untreated control and XPS showed the presence of phosphorus and nitrogen in approximately 1:1 ratio suggesting the presence of phosphate-ester groups on the surface.

EXAMPLE 29

Grafting of HEMA-PC to stainless steel hyperdermic syringe needles

Needles were grafted with HEMA-PC using a procedure based on ceric initiation (analogous to that of Example 25 (method b)) and $Re_2(CO)_{10}$ initiation (analogous to that of Example 28) under various conditions shown below. The variation in the reduction of fibrinogen adsorption is illustrated in the following table:

| Dilution of HEMA in ethanol | HEMA Layer | | | | | |
|---|---|---|---|---|---|---|
| | Static + | | | Flow* | | |
| | Ceric Initiation | | | | | |
| | 30 min | 1 hr | 2 hrs | 30 min | 1 hr | 2 hrs |
| 11:1 Dilution | — | — | 58% | — | — | 79% |
| 5:1 Dilution | 61% | — | 82% | — | — | — |
| 2:1 Dilution | 86% | 81% | 80% | 77% | — | 77% |
| $Re_2(CO)_{10}$ Initiation | | 71% | | | | |

+ no flow of HEMA through needles
*flow of HEMA solution through centre of needles during reaction The table shows the effect of grafting HEMA-PC onto HEMA subbing layers. The conditions for laying down the HEMA layer were altered as indicated. The times refer to the duration of the HEMA reaction. All samples were grafted for 90 minutes with HEMA-PC after the HEMA stage.

EXAMPLE 30

Grafting of HEMA-PC to polyethersulphone filtration membrane

A polyether sulphone membrane was cleaned and placed in a plasma etcher PS0500) and oxygen etched under the following conditions:

| R.F. (%) | 75% |
|---|---|
| Time | 5 minutes |
| $O_2$ (%) | 100% |

The sample was removed and grafted with HEMA-PC using ceric ammonium nitrate initiator and at room temperature conditions analogous to those described in Example 26 in relation to the grafting of HEMA-PC to polypropylene.

EXAMPLE 31

Grafting of HEMA-PC to stainless steel

Stainless steel samples were prepared and silylated as outlined in Example 25 and then grafted with HEMA in methanol using a similar procedure to that in Example 25 method b, with AIBN as initiator in the reaction with HEMA which was carried out at 60° C. for 2 hours. The samples were washed in methanol and a ceric initiated graft was performed using the method of Example 25 with various concentrations of ceric ammonium nitrate and HEMA-PC. Fibrinogen adsorption assays and XPS analysis gave the following results:

| CONDITIONS FOR GRAFTING | REDUCTION RELATIVE TO CONTROL (FIBRINOGEN) | XPS At % | |
|---|---|---|---|
| | | N | P |
| 0.3M HEMA-PC 5 mM CAN | 90% | 4.3% | 4.65% |
| 0.3M HEMA-PC 1 mM CAN | 83% | 3.8% | 4.1% |
| 0.3M HEMA-PC 0.2 mM CAN | 87% | 4.0% | 4.7% |
| 0.1M HEMA-PC 5 mM CAN | 83% | 2.65% | 3.7% |

CAN = ceric ammonium nitrate

EXAMPLE 32

HEMA-PC grafting to stainless steel catheter guidewires

The procedure of Example 28 was used to graft HEMA-PC to stainless steel catheter guidewires. A 75% reduction in fibrinogen adsorption relative to an untreated control was obtained.

EXAMPLE 33

HEMA-PC grafting to glass sample vials

The procedure of Example 27 was used to graft HEMA-PC to glass sample vials. The treated vials showed a 90% adsorption of IgG-HRPO conjugate compared to untreated vials.

EXAMPLE 34

HEMA-PC grafting to stainless steel stents

The procedure of Example 31 with 0.3M HEMA-PC and 5 mM ceric ammonium nitrate was used to graft HEMA-PC to stainless steel stents. An average of 81% reduction in fibrinogen adsorption relative to untreated controls was found. XPS analysis on two points on the stents gave:

| | N (at %) | P (at %) |
|---|---|---|
| Point 1 | 2.1 | 2.4 |
| Point 2 | 1.5 | 1.9 |

EXAMPLE 35

Grafting of HEMA-PC to stainless steel ($Mo(CO)_6$ initiated)

A procedure analogous to that of Example 28 was used to graft HEMA-PC to stainless steel except that $Mo(CO)_6$ was used rather than $Re_2(CO)_{10}$ and the graft reaction was carried out under refluxing in ethanol for 30 minutes.

Reference Example 1

Preparation of 2(methacryloyloxyethyl)-2'(trimethylammonium)ethyl phosphate inner salt HEMA-PC)

The method is according to Umeda et al., (Makromol Chem., Rapid Commun., 3, no. 7. 1982). An analogous procedure, also usable to provide HEMA-PC, has been described in WO-A-92/07885 (incorporated herein by reference).

The general reaction scheme is as follows:

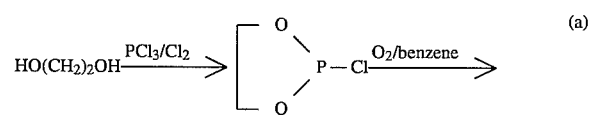

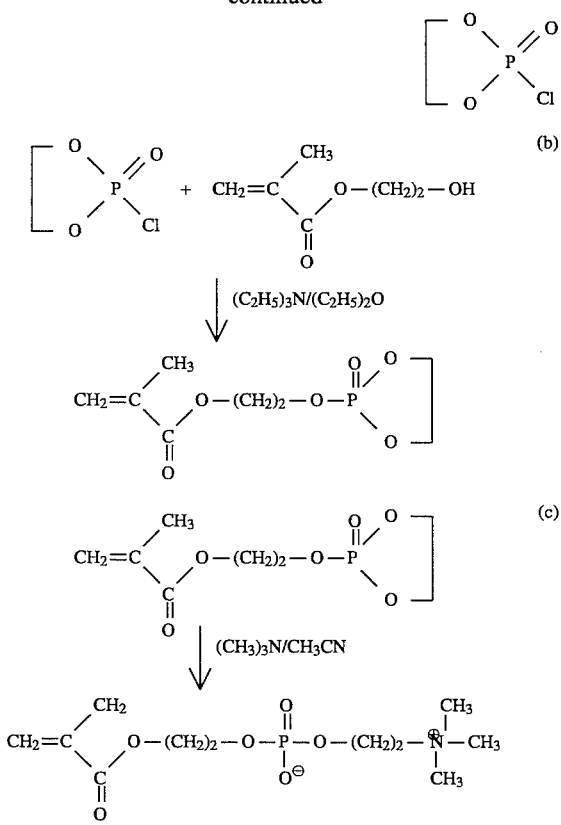

(a) Preparation of 2-chloro-2-oxo-1,3,2-dioxaphospholane

Ethylene glycol was reacted with phosphorus trichloride in dichloromethane to give 2-chloro-1,3,2-dioxaphospholane in 65% yield (Lucas et al., J. Am. Chem. Soc. 72, 5491 (1950)). The product was then oxidised with oxygen to give 2-chloro-2-oxo-1,3,2-dioxaphospholane in 95% yield (Edmundson, Chem. Ind. (London), 1962, 1828).

(b) Preparation of 2-(2-oxo-1,3,2-dioxaphospholan-2-yloxy)ethyl methacrylate

The 2-chloro-2-oxo-1,3,2-dioxaphospholane prepared in step (a) was reacted with 2-hydroxyethyl methacrylate to give 2-(2-oxo-1,3,2-dioxaphospholan-2-yloxy)ethyl methacrylate, as follows: Into a thoroughly dried 500 cm³ three-necked round bottomed flask equipped with a mechanical stirrer, drying tube and dropping funnel were placed 2-hydroxyethyl methacrylate (20.0 g, 0.154 mol) and triethylamine (15.6 g, 0.154 mol) was added slowly to the stirred solution, maintained at −20° C. to −15° C., over a period of 0.5 hr, whereupon triethylamine hydrochloride began to precipitate from the solution.

The solution was then allowed to warm up to a temperature of 5° to 10° C., at which it was maintained for 2 hours.

The precipitate which had formed was then filtered off and washed with diethyl ether (30 cm³). The filtrate and the diethyl ether solutions were evaporated under reduced pressure in a stream of nitrogen, and then diethyl ether (25 cm³) was added to the residue. The mixture was shaken for 1 minute and then filtered with a glass filter to remove a small amount of triethylamine hydrochloride. The filtrate was evaporated under reduced pressure with a stream of nitrogen for 1.5 hours. 2-(2-oxo-1,3,2-dioxaphospholan-2-yloxy)ethyl methacrylate was obtained (35.9 g, 99% yield) as colourless liquid.

(c) Preparation of 2-(methacryloyloxyethyl)-2'(trimethylammonium)ethyl phosphate inner salt Into a glass pressure bottle (300 cm³), were placed 2-(2-oxo-1,3,2-dioxaphospholan-2-yloxy)ethyl methacrylate (10.0 g, 42 mmol) prepared in step (b) and dry acetonitrile (60 cm³). The pressure bottle was cooled in cold water and then trimethylamine (2.5 g, 42 mmol) was rapidly added to the cold solution. The pressure bottle was closed and then shaken in a thermostat maintained at 55° C. for 2 hours. The reaction mixture was then allowed to come to room temperature and to stand overnight, and was shaken again at 55° C. for 2 hours. The reaction mixture was cooled down in water to 10° C. and it was rapidly filtered with filter paper. The filtrate was evaporated under reduced pressure with a stream of nitrogen for 2 hours to afford the product (12.3 g, 98%) as a colourless viscous liquid which crystallised on standing in a freezer. The product could be purified by preparative liquid chromatography.

Reference Example 2

Preparation of 1[4(4'-vinylbenzyloxy)butane]-2"-(trimethylammonium)ethyl phosphate inner salt, (a) 4-Hydroxy-1(4'-vinylbenzyloxy)butane Butanediol (40 ml; 40.68 g; 0.452 mol) was stirred in a 100 ml round bottomed flask, and treated portionwise with potassium butoxide (17.60 g; 0.144 mol). The initial reaction was exothermic. The reaction mixture was stirred for 1.5 hours at room temperature. The resulting cloudy solution was then treated with chloromethyl styrene (20.00 g; 0.131 mol). The styrene formed an upper, pale green layer, (the colouration being due to the presence of inhibitor), whose colour darkened considerably on the addition of 18-crown-6 (0.49 g; 1.86×10⁻³ mole). The flask was stoppered, protected from light, and stirred for 28 hours at room temperature. The mixture was then poured into water (120 ml) and extracted with dichloromethane (4×50 ml). The combined organic extracts were dried (MgSO₄) and evaporated to give viscous yellow oil 932.7 g). This oil was distilled from a small amount of CuCl to give a product showing some impurities on tlc. The oil was then chromatographed on silica gel, initially eluting with dichloromethane/petrol (1:1) to remove the impurities. The product was the eluted off the column with ethyl acetate/petrol (1:1). Evaporation of the solvent gave a colourless oil, which was distilled to give the desired styrylbutyl alcohol as a colourless oil b.pt. 150°–152°/0.4 mbar. Yield 18.70 g; 69.2%

Nmr (60 MHz: CDCl₃) 1.55 (m,4H C—CH₂—C); 3.50 (m, 5H, 1H exch.; O—CH₂—, O—H), 4.45 (s,2H; Ar—CH₂—), 5.50 (dd, 2H, vinylic), 6.75 (dd, vinylic), 7.40 (m, 4H, Ar—H). IR 3402, 2938, 2888, 1631, 1602, 1582, 1511, 1480, 1445, 1382, 1320, 1116, 1063, 920, 907, 827, 801, 716, and 667 cm⁻¹

(b) 4(2-Oxo-1,3,2-dioxaphospholane-2-yloxy)-1(4'-vinylbenyloxy)butane

4-Hydroxy-1(4'-vinylbenzyloxy)butane (5) (10.03 g; 48.69 mmol) and dried triethylamine (4.92 g, 48.69 mmol) were dissolved in dry diethyl ether (150 ml) and the resulting solution placed in a rigorously dried flask. The solution was cooled to −30° and 2-chloro-2-oxo-1,3,2-dioxaphospholane (6.94 g; 48.69 mmol) added dropwise over 30 minutes, the temperature being held at −30°. The reaction mixture was then stirred for a further 2 hours, during which time the temperature was allowed to rise to 10°. The mixture was filtered and the precipitate washed with dry ether. The filtrate was evaporated (20°/21 mm) to give a cloudy oil. The residue was shaken with 50 ml of dry ether and refiltered. Evaporation of the filtrate gave the product as a viscous yellow oil (13.73 g; 90.4%).

TLC (eluting with 10% MeOH/90% dichloromethane) showed one major spot, which stained with acid molybdate reagent (Rf 0.61), IR (thin film) 3458, 2945, 2917, 2860, 1630, 1602, 1581, 1475, 1419, 1363, 1283, 1103, 1032, 820, 842, 807, 800, 715, 610 and 421 cm$^{-1}$.

(c) 1[4(4'-vinylbenzyloxy)butane]-2"(trimethylammonium-)ethyl phosphate inner salt Trimethylamine (2.00 g, 33.9 mmol) was distilled into a reaction vessel, and frozen with liquid nitrogen. A solution of the 4(2-oxo-1,3,2-dioxaphospholane-2-yloxy)-1-(4'-vinylbenyloxy)butane (10.00 g, 32.1 mmol) in anhydrous acetonitrile (40 ml) was then added to the reaction vessel, which was then sealed and placed in a thermostated water bath (50° for 50 hours). The reaction vessel was then cooled to room temperature, opened, and the reaction mixture evaporated to about half its original volume (21 mm pressure). The concentrated solution was then stirred at room temperature, whilst anhydrous ether (200 ml) was added dropwise to precipitate the product as a viscous oil. The mixture was then left for several hours at −10°. The product was collected by decanting off the supernatent solid. TLC (eluting with methanol/dichloromethane 1:1) showed one major spot at Rf 0.0–0.1 which stained with both Dragendorffs reagent and acid molybdate.

The overall reaction scheme is illustrated below.

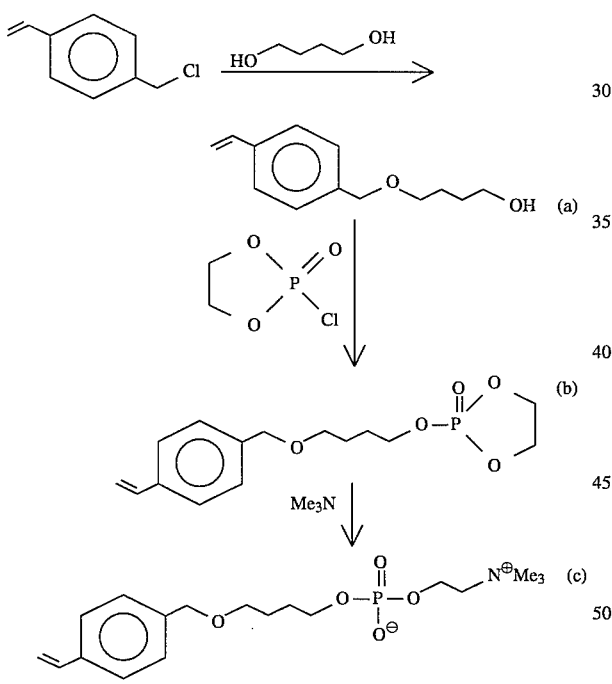

We claim:

1. A graft polymer obtained by grafting a polymer substrate with a compound of the formula (IIA):

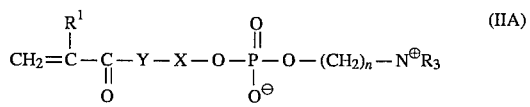

in which the groups R are the same or different and each is a straight or branched $C_1$–$C_4$ alkyl group;

X is a straight or branched $C_1$–$C_{20}$ alkylene group, optionally containing one or more carbon-carbon double or triple bonds, ether linkages or aryl groups; the aryl groups being unsubstituted or substituted by one or more $C_{1-4}$ alkyl groups;

n is from 2 to 4;

$R^1$ is hydrogen or straight or branched $C_1$–$C_4$ alkyl, and Y is —O— or —NR$^2$— where $R^2$ is hydrogen or straight or branched $C_1$–$C_4$ alkyl and the substrate has halogen substituted groups which can form free radicals, the grafting reaction being initiated by formation of a radical on the substrate at the halogen substituted group followed by reaction of the radical with the ethylenic group of compound (IIA).

2. A polymer according to claim 1, which is obtained by grafting with a compound of formula (IIA), in which X is a $C_1$–$C_{20}$ alkylene group.

3. A polymer according to claim 1 or 2, which is obtained by grafting a compound of formula (IIA) in which n is 2 and each of the groups R is methyl.

4. A polymer according to claim 1, which is obtained by radical initiated polymerization of the compound of formula (IIA) and optionally a diluent comonomer, the reaction polymerization being initiated by formation of a radical at the substrate using a metal carbonyl initiator.

5. A polymer according to claim 4, in which the compound of formula (IIA) is 2(methacryloyloxy)-ethyl-2'(trimethylammonium)ethyl phosphate inner salt.

6. A shaped article having one or more surfaces comprising a graft polymer as claimed in claim 1.

7. An article according to claim 6, which is a biomedical device, contact lens or blood-contacting device.

8. A process for producing a graft polymer comprising the steps of:

(i) providing a polymer having halogen atom substituents;

(ii) reacting the polymer with an initiator such that a free radical is formed on the polymer at the halogen substituent;

(iii) initiating graft polymerization at the free radical formed in step (ii) of a compound of formula (IIA):

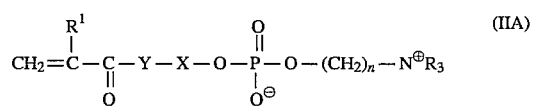

in which the groups R are the same or different and each is a straight or branched $C_1$–$C_4$ alkyl group;

X is a straight or branched $C_1$–$C_{20}$ alkylene group, optionally containing one or more carbon-carbon double or triple bonds, ether linkages or aryl groups; the aryl groups being unsubstituted or substituted by one or more $C_{1-4}$ alkyl groups;

n is from 2 to 4, $R^1$ is hydrogen or straight or branched $C_1$–$C_4$ alkyl, and Y is —O— or —NR$^2$— where $R^2$ is hydrogen or straight or branched $C_1$–$C_4$ alkyl; and (iv) recovering the grafted product.

9. A process according to claim 8 in which, X is a $C_1$–$C_{20}$ alkylene group.

10. A process according to claim 8 in which polymerization is initiated at hydroxyl groups on the polymer substrate by a cerium (IV) salt or at halogen atoms on the polymer substrate by molybdenum hexacarbonyl or dirhenium decacarbonyl.

11. A process according to claim 8 in which the polymer substrate is in solid or gel form during the grafting reaction.

12. A process according to claim 11 in which the polymer substrate forms the surface of a shaped article.

13. A process for producing a graft polymer, comprising the steps of:
   (i) providing a polymer substantially free of reactive groups;
   (ii) subjecting the polymer to oxidation by a treatment selected from the group consisting of oxygen plasma treatment, reaction with a peracid, reaction with a hypohalite, and reaction with ozone, to introduce hydroxyl groups onto the polymer;
   (iii) reacting the hydroxyl groups with an initiator to form a free radical;
   (iv) initiating graft polymerization at the free radical of a compound of the formula (IIA):

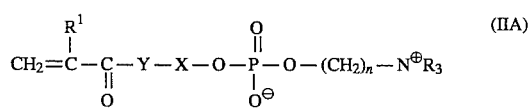

in which the groups R are the same or different and each is a straight or branched $C_1$–$C_4$ alkyl group;
   X is a straight or branched $C_1$–$C_{20}$ alkylene group;
   n is from 2–4,
   $R^1$ is hydrogen or a straight or branched $C_1$–$C_4$ alkyl; and
   Y is —O— or —$NR^2$— where $R^2$ is hydrogen or a straight or branched $C_1$–$C_4$ alkyl; and
   (v) recovering the grafted product.

14. A process according to claim 13, in which the polymer substrate is selected from the group consisting of: polyvinyldifluoride, a polypropylene, a polyamide, a polyimide, a polyurethane, a polyimine, and a polyether sulphone.

15. A process according to claim 13 in which radical polymerisation is initiated by a cerium (IV) salt.

16. A process according to claim 13, in which Y is —O—.

17. A process according to claim 13, in which X is a $C_1$–$C_{20}$ alkylene group.

18. A process according to claim 13, in which the compound of formula (IIA) is 2(methacryloyloxy)-ethyl-2'(trimethylammonium)ethyl phosphate inner salt.

19. A process for producing a graft polymer, comprising the steps of:
   (i) providing a substrate having a surface;
   (ii) laying down a subbing layer of a subbing polymer;
   (iii) reacting the polymer with an initiator such that a free radical is formed on the polymer;
   (iv) initiating graft polymerization at the free radical of a compound of the formula (IIA):

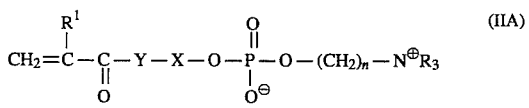

in which the groups R are the same or different and each is a straight or branched $C_1$–$C_4$ alkyl group;
   X is an aryl group or straight or branched $C_1$–$C_{20}$ alkylene group, optionally containing one or more carbon double or triple bonds, ether linkages or aryl groups; the aryl groups being unsubstituted or substituted by one or more $C_1$–$C_4$ alkyl;
   n is from 2–4,
   $R^1$ is hydrogen or a straight or branched $C_1$–$C_4$ alkyl; and
   Y is —O— or —$NR^2$— where $R^2$ is hydrogen or a straight or branched $C_1$–$C_4$ alkyl; and
   (v) recovering the grafted product.

20. A process according to claim 19, in which Y is —O—.

21. A process according to claim 19, in which X is a $C_1$–$C_{20}$ alkylene group.

22. A process according to claim 19, in which the compound of formula (IIA) is 2(methacryloyloxy)-ethyl-2'(trimethylammonium)ethyl phosphate inner salt.

23. A process according to claim 19, in which the subbing polymer is selected from the group consisting of halogenated polyethylene imines, poly(hydroxyalkyl(alk)acrylates) and poly(trialkoxysilylalkyl(alk)acrylates).

* * * * *

UNITED STATES PATENT AND TRADEMARK OFFICE
CERTIFICATE OF CORRECTION

PATENT NO.   : 5,453,467
DATED        : September 26, 1995
INVENTOR(S)  : BAMFORD et al.

It is certified that error(s) appears in the above-identified patent and that said Letters Patent is hereby corrected as shown below:

On the title page, change item "[22] Filed: April 28, 1994" to --[22] PCT Filed: August 28, 1992--, and insert --[86] PCT No.:      PCT/GB92/01580
    § 371 Date:      April 28, 1994
    § 102(e) Date:   April 28, 1994
 [87] PCT Pub. No.:  WO 93/05081
    PCT Pub. Date:   March 18, 1993--.

Signed and Sealed this

Twentieth Day of August, 1996

BRUCE LEHMAN

*Attest:*

*Attesting Officer*         *Commissioner of Patents and Trademarks*